US010441209B2

(12) United States Patent
Strader et al.

(10) Patent No.: US 10,441,209 B2
(45) Date of Patent: Oct. 15, 2019

(54) ANTIGEN REGIONAL TESTING KIT

(71) Applicant: ROCA MEDICAL LTD., London (GB)

(72) Inventors: James Strader, Austin, TX (US); Jovan Hutton Pulitzer, Frisco, TX (US)

(73) Assignee: ROCA Medical Ltd., London (GB)

( * ) Notice: Subject to any disclaimer, the term of this patent is extended or adjusted under 35 U.S.C. 154(b) by 206 days.

(21) Appl. No.: 15/425,863

(22) Filed: Feb. 6, 2017

(65) Prior Publication Data

US 2017/0224269 A1 Aug. 10, 2017

Related U.S. Application Data

(60) Provisional application No. 62/291,433, filed on Feb. 4, 2016.

(51) Int. Cl.

| | |
|---|---|
| ***A61F 17/00*** | (2006.01) |
| ***A61B 5/00*** | (2006.01) |
| ***A61K 49/00*** | (2006.01) |
| ***A61B 10/00*** | (2006.01) |
| *A61B 17/20* | (2006.01) |

(52) U.S. Cl.

CPC ............ *A61B 5/443* (2013.01); *A61B 5/6848* (2013.01); *A61B 10/0035* (2013.01); *A61K 49/0006* (2013.01); *A61B 17/205* (2013.01)

(58) Field of Classification Search

CPC ........ A61B 50/00; B65D 69/00; B65D 71/00; B65D 77/00

USPC .......................................................... 206/570

See application file for complete search history.

(56) References Cited

U.S. PATENT DOCUMENTS

| | | | | |
|---|---|---|---|---|
| 3,627,122 A * | 12/1971 | Garbe, Jr. | A47B 87/02 | 116/308 |
| 3,743,088 A * | 7/1973 | Henkin | A61B 5/00 | 116/201 |
| 3,899,298 A * | 8/1975 | Szczesniak | G01N 33/539 | 206/568 |
| 5,104,620 A * | 4/1992 | Wiley | A61B 5/411 | 422/430 |
| 5,143,210 A * | 9/1992 | Warwick | A61B 10/0096 | 206/499 |

(Continued)

OTHER PUBLICATIONS

PCT: European Patent Office Searching Authority, International Search Report and Written Opinion of PCT/IB2015/001330 (related application), dated Oct. 5, 2015, 14 pgs.

(Continued)

*Primary Examiner* — King M Chu

(74) *Attorney, Agent, or Firm* — Gregory M. Howison

(57) ABSTRACT

A method for administering tests using a regional antigen testing kit is provided. The method comprises providing the regional antigen testing kit, extracting a predetermined amount of concentrated antigen from one of a plurality of concentrated antigens, dispensing the predetermined amount of concentrated antigen into a corresponding one of a plurality of wells, as indicated by visual indicia, repeating the extracting and dispensing steps until a desired number of the plurality of wells contain concentrated antigen, providing a prick tester having a plurality of needles extending thereon, aligning the plurality of needles of the prick tester with the plurality of wells, inserting each of the plurality of needles of the prick tester into one of the plurality of wells, and applying the plurality of needles of the prick tester to the skin of a patient to elicit a potential response.

8 Claims, 17 Drawing Sheets

(56) References Cited

U.S. PATENT DOCUMENTS

| | | | | |
|---|---|---|---|---|
| 5,848,700 | A * | 12/1998 | Horn | A61F 17/00 206/570 |
| 6,488,937 | B1 | 12/2002 | Smits | |
| 2003/0082212 | A1 | 5/2003 | Smits | |
| 2006/0020514 | A1 | 1/2006 | Yered | |
| 2006/0212318 | A1 | 9/2006 | Dooley et al. | |
| 2009/0152159 | A1 * | 6/2009 | Beeman | A45C 11/00 206/570 |
| 2009/0169602 | A1 | 7/2009 | Senti et al. | |
| 2010/0326868 | A1 * | 12/2010 | McClain | B65D 23/085 206/459.5 |
| 2013/0020227 | A1 * | 1/2013 | Stack | A61J 1/065 206/570 |

OTHER PUBLICATIONS

Baumann L.S. et al., "Lip Silicone Granulomatous Foreign Body Reaction Treaded with Aldara (Imiquimod 5%)", Dermatologic Surgery 20030401 US, vol. 29, No. 4, Apr. 1, 2003 (Apr. 1, 2003), pp. 429-432, XP002745005, ISSN: 1076-0512, p. 429, left-hand column, paragraph middle.

Prieto-Garcia Alicia et al: "Autoimmune Progesterone Dermatitis: Clinical Presentation and Management with Progesterone Desensitization for Successful In Vitro Fertilization", Fertility and Sterility, vol. 95, No. 3, Mar. 2011 (Mar. 2011), pp. 1121.e9-1121.e13, XP28147753, p. 1121.e9, left-hand column p. 1121.e12, left-hand column, paragraph top.

Cox et al., J. Allergy Clin. Immunol. 2011; 127(1 ):S1-S55.

El Maghraby et al. Eur. J. Pharma. Sci. 2008; 34:203-222 Apr. 18, 2008.

PCT: European Patent Office Searching Authority, International Search Report and Written Opinion of PCT/IB2016/001332 (related application), dated Nov. 24, 2016, 13 pgs. Nov. 24, 2016.

E. Alvarez-Cuesta et al., "Subcutaneous immunotherapy", Allergy, vol. 61, No. s82, Oct. 2006 (Oct. 2006), pp. 5-13, XP055319495, UK Oct. 1, 2006.

* cited by examiner

ANTIGEN REGIONAL TESTING KIT

CROSS-REFERENCE TO RELATED APPLICATIONS

This application claims the benefit of U.S. Provisional Application No. 62/291,433, filed on Feb. 4, 2016, entitled ANTIGEN REGIONAL TESTING KIT, which is herein incorporated by reference in its entirety.

TECHNICAL FIELD

This application is generally related to the delivery of immunomodulators to a patient.

BACKGROUND

Immunotherapy (IT) is recognized as one of the most curative treatment for allergies. By exposing the immune system to slowly increasing concentrations of immunomodulators such as an allergen or antigen, it will eventually stabilize and regain control the portion that is hypersensitive to the allergen or antigen. In general, immunotherapy is the "treatment of disease by inducing, enhancing, or suppressing an immune response." Immunotherapies designed to elicit or amplify an immune response are classified as activation immunotherapies, while immunotherapies that reduce or suppress are classified as suppression immunotherapies. The active agents of immunotherapy are collectively called immunomodulators. They are a diverse array of recombinant, synthetic and natural preparations, often cytokines.

Immunotherapy involved in the treatment of allergies is a type of suppression immunotherapy, often termed desensitization or hypo-sensitization. This is compared with allergy treatments such as antihistamines or corticosteroids which treat only the symptoms of allergic disease. Immunotherapy is the only available treatment that can modify the natural course of the allergies, by reducing sensitivity to the immunomodulators such as antigens or allergens. An antigen and an allergen can both cause one's immune system to respond. An allergen is an antigen, but not all antigens are allergens. An antigen is any substance that is capable of causing one's immune system to produce antibodies. They are typically organic, or living, produced proteins. An allergen is any antigen that causes an allergic reaction. A non-allergen antigen could be a bacteria, virus, parasite, or fungus that causes an infection. This could also be something else that causes antibody immune system response, like toxins, chemicals, tissue cells involved in transplants or blood cells from a blood transfusion. An allergen is an environmentally produced substance that causes an allergic reaction, although the substance may not be harmful. Allergens cause no reactions in some individuals, while possibly causing a hypersensitive reaction in others. Common allergens include such things as pollen, plants, smoke, feathers, perfumes, dust mites, toxic mold, food, drugs, animal dander, and insect bites and stings.

The exact mechanisms of how IT works are not fully understood, but they involve shifting a patient's immune response from a predominantly "allergic" T-lymphocyte response to a "non-allergic" T-lymphocyte response.

Current accepted processes for performing allergy immunotherapy include injecting immunomodulator matter in the form of antigen material into patient subjects. This is referred to as subcutaneous immunotherapy (SCIT), requiring a patient to visit a doctor's office for weekly injections. It is very expensive and time-consuming. A second technique, sublingual immunotherapy (SLIT), involves the application of allergy extracts (antigens), and allergens placed into a pill form and swallowed by the patient or disposed in "allergy drops" which are placed under the tongue for the allergens/antigens to be absorbed into the oral mucosa. Transdermal patches may have been used without much success and mostly were used for patch testing to see if a patient reacts to various chemicals or allergens.

Of the people who start traditional subcutaneous injected immunotherapy (SCIT), 90% fail to complete their therapy due to needle fatigue and not being able to see a doctor in their office once or more per week for several years. Further, doctors charge for every one of those visits. Further, doctors trained to give injections for allergies are concentrated in high population and upper middle class places. People in rural areas and people who do not live in upper middle class areas cannot get to an allergist for shots. Consider an inner city kid having to ride public transportation and pay a high copay just to get a high risk injection if an alternative therapy were available!

Allergies are also linked to depression and suicide and are among the top ten reasons for missed work and lost productivity. Lastly, allergies and asthma result in billions of dollars in lost productivity and healthcare costs among the 90% of allergy patients that either never get immunotherapy or fail immunotherapy delivered under its current administration methods.

SUMMARY

In one aspect thereof, a method for administering tests using a regional antigen testing kit is provided. The method comprises providing the regional antigen testing kit, the regional antigen testing kit including a first portion hingedly coupled to a second portion, allowing for the regional antigen testing kit to be opened and closed in a clamshell configuration, wherein the first portion has disposed therein a plurality of concentrated antigens, each one of the plurality of concentrated antigens being disposed in a sealable container, wherein the first portion further has disposed therein a first control material and a second control material, the first control material and the second control material each being disposed in a sealable container, wherein the second portion includes a plurality of wells capable of receiving an amount of concentrated antigen, and wherein the first portion and the second portion include visual indicia to correspond each of the plurality of concentrated antigens with one of the plurality of wells. The method further comprises extracting a predetermined amount of concentrated antigen from one of the plurality of concentrated antigens, dispensing the predetermined amount of concentrated antigen into a corresponding one of the plurality of wells, as indicated by the visual indicia, repeating the extracting and dispensing steps until a desired number of the plurality of wells contain concentrated antigen, providing a prick tester having a plurality of needles extending thereon, aligning the plurality of needles of the prick tester with the plurality of wells, inserting each of the plurality of needles of the prick tester into one of the plurality of wells, and applying the plurality of needles of the prick tester to the skin of a patient to elicit a potential response.

In another embodiment, the regional antigen testing kit further includes a third portion having disposed therein a plurality of sealable containers containing a dilutant.

In another embodiment, the method further comprises mixing the extracted predetermined amount of concentrated antigen with the dilutant from one or more of the plurality of sealable containers to create a diluted antigen, and wherein the step of dispensing instead includes dispensing an amount of the diluted antigen into one of the plurality of wells corresponding to the antigen contained within the diluted antigen.

In another embodiment, the dilutant comprises a saline solution.

In another embodiment, the dilutant comprises a glycerol solution.

In another embodiment, the method is carried out in a sterile environment.

In another embodiment, the first control material is water.

In another embodiment, the second control material is a histamine.

In another embodiment, the regional antigen testing kit includes a National Drug Code (NDC) associated with the regional antigen testing kit.

In another embodiment, the plurality of concentrated antigens corresponds to antigens found in a particular geographic area.

In another embodiment, the regional antigen testing kit includes one of a plurality of National Drug Codes (NDCs), the one of the plurality of NDCs being assigned to the antigen regional testing kit based on the particular geographic area.

In another aspect thereof, a regional antigen testing kit is provided. The regional testing kit comprises a first portion having disposed therein a plurality of concentrated antigens, each one of the plurality of concentrated antigens being disposed in a sealable container, and the first portion further having disposed therein a first control material and a second control material, the first control material and the second control material each being disposed in a sealable container, a second portion hingedly coupled to the first portion, allowing for the regional antigen testing kit to be opened and closed in a clamshell configuration, wherein the second portion includes a plurality of wells capable of receiving an amount of concentrated antigen, and visual indicia disposed on the first portion and the second portion, in order to correspond each of the plurality of concentrated antigens with one of the plurality of wells.

In another embodiment, the regional antigen testing kit further comprises a third portion having disposed therein a plurality of sealable containers containing a dilutant.

In another embodiment, the dilutant comprises a saline solution.

In another embodiment, the dilutant comprises a glycerol solution.

In another embodiment, the first control material is water.

In another embodiment, the second control material is a histamine.

In another embodiment, the regional antigen testing kit includes a National Drug Code (NDC) associated with the regional antigen testing kit.

In another embodiment, the plurality of concentrated antigens corresponds to antigens found in a particular geographic area.

In another embodiment, the regional antigen testing kit includes one of a plurality of National Drug Codes (NDCs), the one of the plurality of NDCs being assigned to the antigen regional testing kit based on the particular geographic area.

BRIEF DESCRIPTION OF THE DRAWINGS

For a more complete understanding, reference is now made to the following description taken in conjunction with the accompanying Drawings in which.

DETAILED DESCRIPTION

Figure 1:
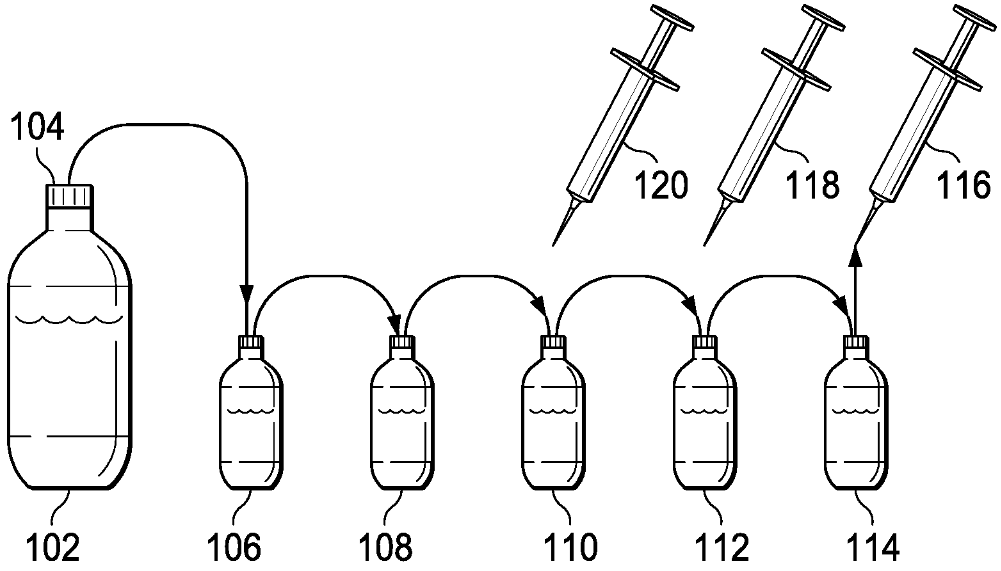
FIG. 1 illustrates a diagrammatic view of a dilution sequence of diluting a concentrated antigen extract.

Referring now to the drawings, wherein like reference numbers are used herein to designate like elements throughout, the various views and embodiments of an antigen regional testing kit are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated a depiction of a typical technique for diluting immunomodulators such as antigens, as one example. Preparation of a diluted antigen is performed first by receiving a bottle of extract concentrates from an approved vendor. These are formulated in a given weight/volume (w/v) format with a given antigen associated therewith. For typical antigens such as those associated with the cat antigen, these are relatively well controlled. Typically, a vendor will provide an extract for a single antigen or allergen. Allergens such as pollen and the such are not as well controlled due to the technique for collecting such. In any event, there are typically very few approved vendors for these extracts and allergist typically receives these vendor provided concentrates in a sufficient quantity to make the necessary diluted solution.

Allergen extract is typically comprised of a non-allergenic material, a non-allergenic protein, and an allergenic protein. The extraction solutions can be aqueous containing saline and phenol which could be a glycerinated solution. The allergen is added, the units of measure are sometimes referred to as "AU" for "allergy units," typically used for mites. These are referred to as "AU/mL." For such things as grass and cats, the term "BAU" is used for "bioequivalent units." For other allergens, the terminology is, for example, 1:20 w/v, which stands for 1 g source material per 20 mL of fluid. The relationship between BAU and 1:20 w/v depends upon the extract. In any event, there is a defined amount of extract contained within the concentrate.

When concentrated extracts are formulated by an authorized vendor, they are typically provided in standardized versions and non-standardized versions. In standardized versions, they typically are provided in a 50% glycerin dilutant. They can either be a single allergen extract, or they can be a mix. For example, one can obtain a "9 Southern Grass Mix (concentrate)" which contains equal parts of: 2 Bermuda at 10,000 BAU/mL, P27 7 Grass at 100,000 BAU/mL, and 15 Johnson at 1:20 w/v. For non-standardized extracts, these are typically provided in either a glycerin dilutant or an aqueous dilutant such as saline. They can be a single extract or a mix. Thus, whenever a concentrated extract is referred to hereinbelow, this refers to a formulation that is provided by an authorized vendor that can be diluted in accordance with the processes described hereinbelow. These are typically provided in the 50 mL bottles with a needle compatible.

Referring back to FIG. 1, the extract concentrate is disposed in a bottle 102. This is a sterile concentrate that has an injection stoppered top 104. There are provided a plurality of five 5 mL sterile injection stoppered bottles 106, 108, 110, 112 and 114, although there could be more, and the bottles or containers could be larger than 5 mL. Each of these bottles has disposed therein a defined amount of dilutant, depending upon what the final dilutant is required to be. Typically, the amount of dilutant is 4.5 mL. The procedure is to, first, extract a defined amount of the concentrated extract from the bottle 102 and dispose it in the bottle 106. This is facilitated by the sterile hypodermic that is inserted through the stopper at the top of the bottle 102 to extract concentrate, and then the hypodermic is inserted to the stopper in the bottle 106 to inject extract from bottle 102 into bottle 106. Typically, the concentration in the concentrated extract bottle 102 is 1:20 w/v. This will result in a dilution of 1:10 in bottle 106. Then, 0.45 mL of the diluted solution from bottle 106 is extracted and inserted into bottle 108, resulting in a 1:100 dilution of the original concentrate in model 108. The process is repeated up to the bottle 114 to provide a solution that is at a dilution of 1:100,000 of the original concentrate. This is a conventional way to provide a selected dilution of the original antigen. However, it should be understood that any concentration level can be provided from one bottle to the next. The purpose of using the sequential bottles is to allow an achievable portion of one bottle to be distributed to the next bottle, rather than trying to extract a very small amount of the initial concentrated extract. Typically, an allergist will then extract from the desired dilution an amount of the diluted antigen for injection percutaneously. Typically, desensitization is achieved by using the most diluted antigen level initially and sequentially moving up to a higher concentration level over time.

Illustrated in FIG. 1 are three hypodermic needles, one selecting a "dose" from bottle 114, and labeled hypodermic 116, a second hypodermic needle 118 for retrieving a dose from bottle 112, a third hypodermic needle 120 for extracting a dose from bottle 110. Each of the hypodermic needles 116, 118 and 120 will contain a different diluted dose. These would typically be separate needles in the event that the allergist or medical professional is injecting a patient. For other purposes, they could be the same needle, depending upon the dose or concentration required. A "dose" is defined by the amount of all the diluted product that would be required for the desired immunotherapy. This is defined by the medical professional. If, for example, bottle 112 were utilized, it may be that 1 mL of diluted solution constituted a "dose." It could be that less than 1 mL constituted a "dose."

In general, the typical distribution chain requires that the allergist or other medical professional purchase the base concentrate and then perform the dilution process. However, this procedure typically requires breaking the seal on the base concentrate bottle and then inserting a needle into the base concentrate bottle for the first dilution step. This occurs multiple times. Thus, multiple needles, each being sterile, can be used one time or, more commonly, a single needle is utilized in association with the base concentrate bottle, with the assumption that, since it does not involve insertion into human flesh, it is still sterile. In any event, this needle must penetrate the rubber stopper seal on the base concentrate bottles multiple times. In fact, these bottles could typically be held upside down and they would leak and, once the seal is broken, there is no sterile cover over the rubber stopper. This is a result of the multiple needle piercings of the rubber stopper. This is also the case with the small 5 mL bottles in that each has to be penetrated at least twice in the higher concentrate bottles. Thus, the last bottle that the allergist has would be a 5 mL bottle, and this bottle would already have one piercing of the rubber stopper seal in order to provide the initial dilution level into the carrier material, such as saline. Thereafter, a patient might be able to receive 5 or 10 doses from that particular bottle, requiring 5 or 10 more piercings of the rubber stopper. During this time, of course, there is no seal over the rubber stopper.

Figure 2:
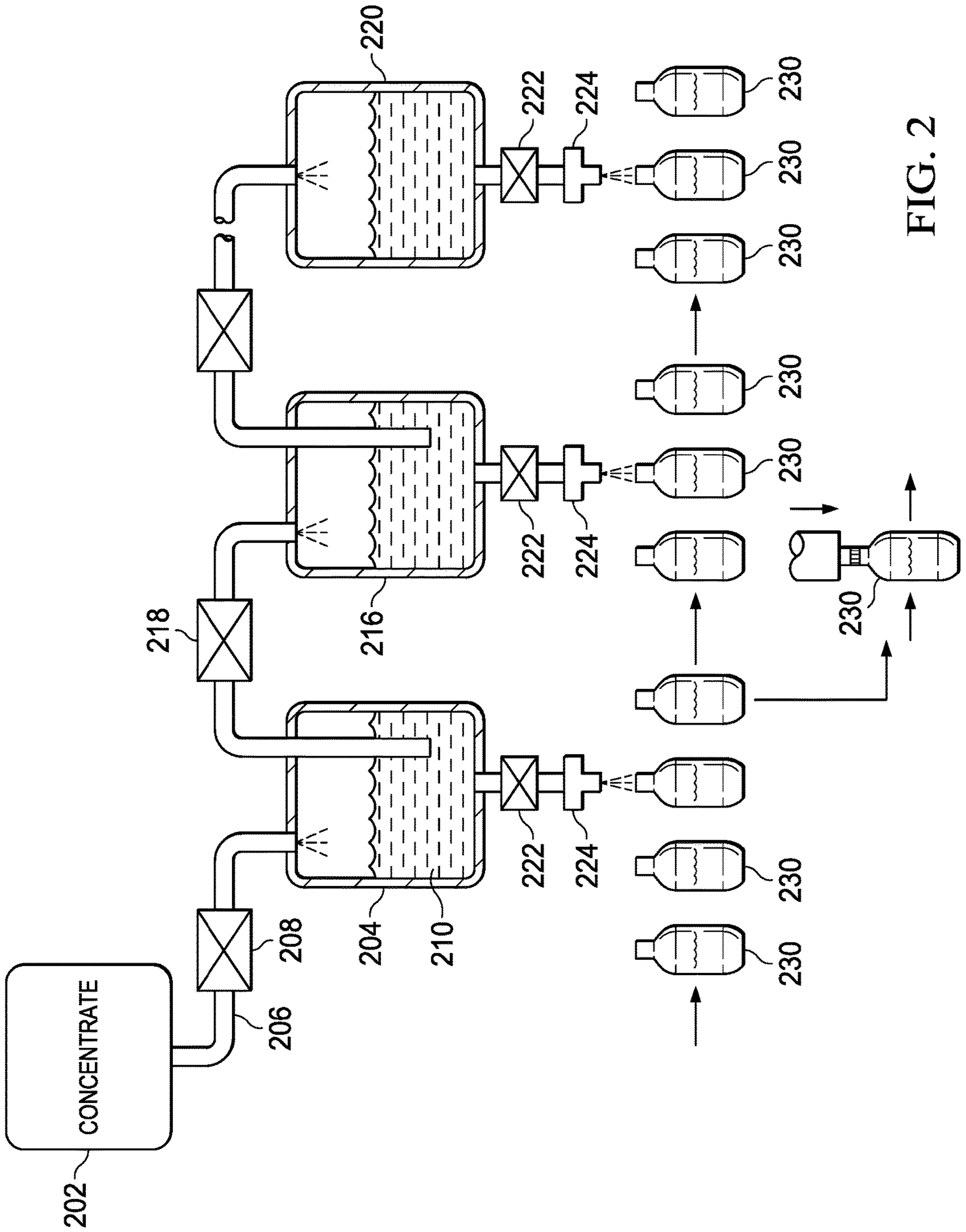
FIG. 2 illustrates a diagrammatic view of a production line for filling distribution bottles.

In order to solve this problem, a process is provided whereby the concentrate bottles are produced from a sterile environment container which already has the dilutant provided thereto. This is illustrated in FIG. 2. In this embodiment, a large bottle of base concentrate 202 is provided at a first concentration. This is then metered into a first dilutant reservoir 204 via a tube 206 and a metering valve 208. The first dilutant container 204 has contained therein a carrier liquid 210 which can be, as described herein below, any of a number of materials, such as saline, glycol and the such. Typically, this depends upon the base carrier material associated with the concentrate 202. By knowing the volume of the material to 10 within the reservoir 204 prior to metering therein of the concentrate 202 with the metering valve 208, a very accurate amount of concentrate 202 can be dispensed within the reservoir 204. This metering valve 208 can be controlled to such a level that a very fine and controlled concentrated level can be defined. At this point in the process, the concentrate 202 defines a "batch" material that, for some allergens, is important. For example, if the allergen was related to pollen or the such, this can vary depending upon the year, the production harvest, the quality of harvest, etc. By defining a batch, and controlling the quality and the concentration level at each step in the dilution level, a very controlled dilution level can be provided for that particular batch.

Once the concentrated level or dilution level in the bottle has been defined, this is then utilized to provide a controlled amount of diluted allergen to a second dilution bottle 216 through a metering valve 218. This is repeated for multiple bottles down the line to a last bottle 220. Thus, there are then provided a plurality of larger vessels with controlled dilution levels at each diluted stage in a sterile environment. Each of these bottles 204, 216, and 220 has associated therewith a control metering valve 222 and a dispensing nozzle 224 that is operable to dispense diluted allergen material into a receptacle. This metering valve 222 and associated nozzle 224 are all approved to interface with an approved bottle.

In the dispensing process, there are provided for each dilution stage a plurality of bottles 230. Each of these bottles has a shape and opening that is approved to be interfaced with the nozzle. Each is passed by the nozzle and an exact amount of diluted material, the allergen, dispense therein. Thereafter, each bottle 230 is then subjected to a Procedure which inserts the rubber stopper and the seal there over. The result is a bottle with a defined dosage amount at a defined concentration level for a known batch of allergen, all of which is a sterile environment. The allergist or medical professional need only then remove this seal, insert the needle through the rubber stopper and extract the appropriate amount of diluted allergen. This particular bottle 230 is designed to be a single dose. Thus, the actual amount of material disposed within the bottle will be approximately 1 mL. Typically, the bottles are 5 mL bottles. In this situation, that 5 mL bottle can be modified to maintain the same size but only provide for a single 1 mL dose. This will be described hereinbelow.

Figure 3:
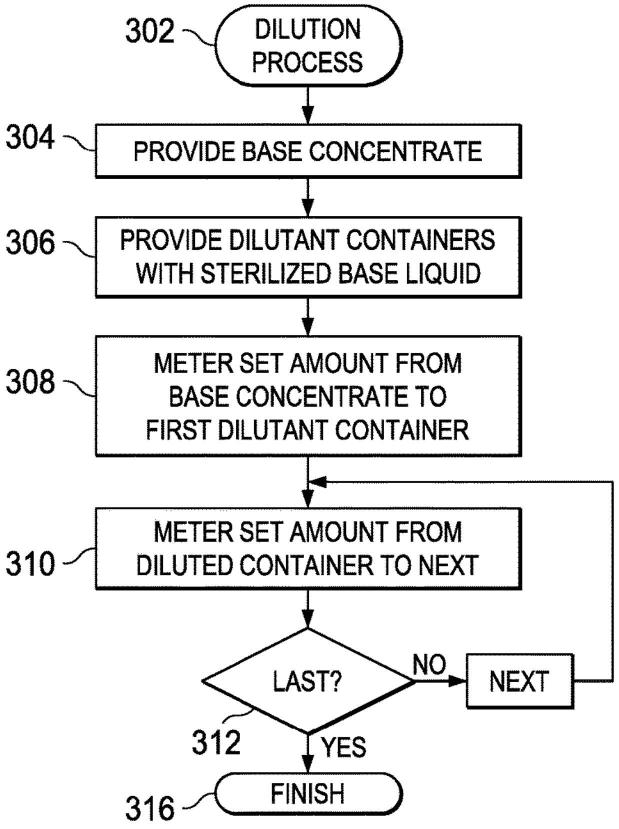
FIG. 3 illustrates a flow chart for the dilution process.

Referring now to FIG. 3, there is illustrated a flowchart for the overall dilution process, which is initiated at a block 302. The process flows to a block 304 to provide the base concentrate. As noted hereinabove, the base concentrate is typically associated with a fixed batch so that it is a well-controlled product, and this is a sterile bottle within a sterile environment, and the size can be larger than typically distributed to an allergist. The process flows to a block 306 wherein the various dilutant containers are provided with a sterilized base liquid such a saline or glycol, depending upon intended final use. The process then flows to block 308 wherein a metered amount of dilutant is passed from the base concentrate vessel to the first dilutant container. The process then flows to a block 310 wherein a metered amount of diluted allergen is transferred from the previous bottle to the next bottle until the last bottle is complete, which is determined at a decision block 312. This will then result in multiple vessels of diluted allergen at the appropriate diluted level for final dispensing. The program then flows to a block 316.

Figure 4:
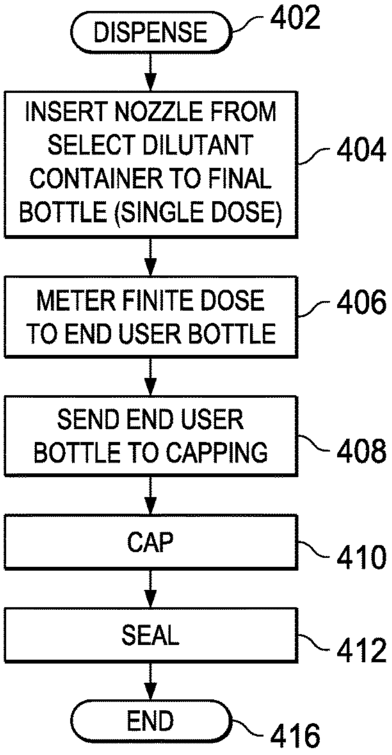
FIG. 4 illustrates a flow chart for the dispensing process.

Referring now to FIG. 4, there is illustrated a flowchart for the dispensing operation, which is initiated at a block 402. The process flows to a block 404 wherein a nozzle is inserted from the select dilutant container or vessel to the final dispensing bottle, typically a single dose bottle. The process then flows to a block 406 to meter a finite dose to the end user bottle. Again, this could be a 1 mL dose in a 5 mL bottle or a 1 mL dose in a 1 mL bottle. The process then flows to a block 408 to send the end user bottle to capping, followed by a process block 410 to dispose a cap on the bottle, this being a rubber seal to allow insertion of the needle there through, and then to a seal block 412 to provide a sterile seal over the bottle and then to a terminate block 416.

Figure 5:
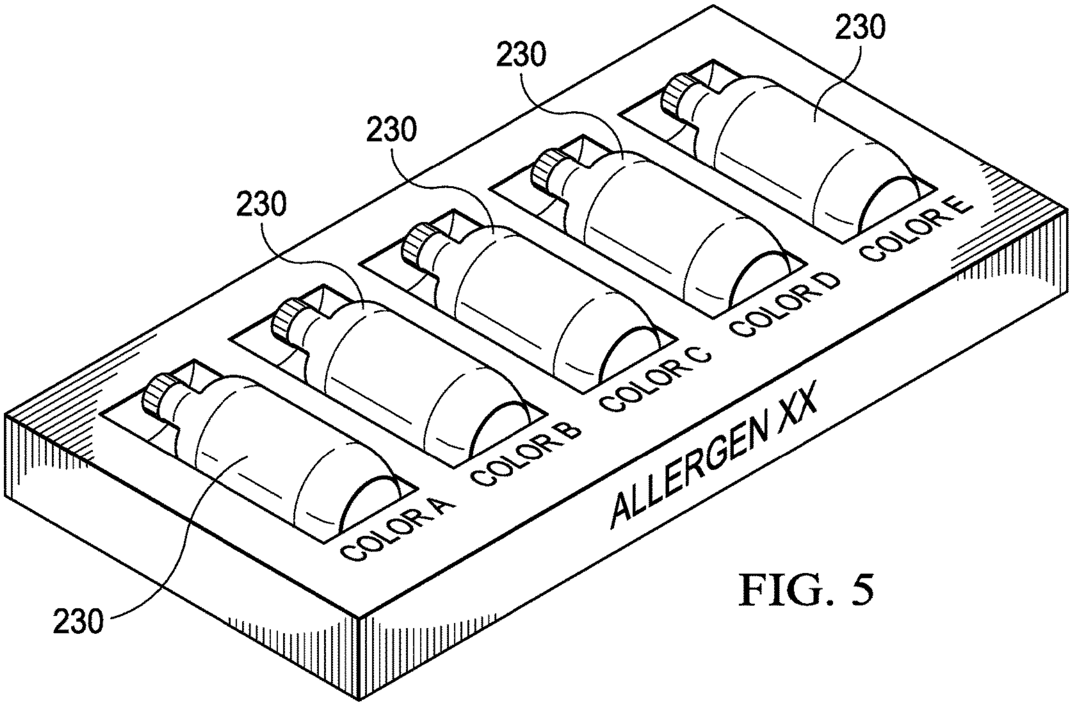
FIG. 5 illustrates a diagrammatic view of a color-coded box with different diluted levels of allergens.

Referring now to FIG. 5, there is illustrated a depiction of a delivery container for the final allergen in the bottles 230. The bottles would typically be controlled such that they would have, for example, a very distinctive color associated with each diluted level. The highest concentration bottle would be a bottle that would have to be carefully dispensed to a patient, as, if not adequately desensitized to the allergen, this could result in anaphylactic shock to the patient. Thus, it is important that the correct dose at the correct dilution level is administered at a particular time. This color coding process for any type of identification process clearly presents to the medical professional some clear indication of the concentrated level of allergen. Typically, these allergens will be provided in a kit form. For example, it may be that a patient would require the lowest concentrate level of the allergen three times per week for two weeks, followed by the next concentrated level of allergen two times per week for one week, etc. Thus, the various diluted levels of concentrate would be provided in single-dose bottles to, for example, a pharmacy, which would dispense the particular dosages. The first thing is that they would be from a common batch and they would be provided to the patient in the appropriate presentation. For example, the patient might receive a first box of six bottles 230 at the lowest concentrate level for the first two weeks. The pharmacist then would provide the second part of the prescription for the second level in the form of two bottles of concentrate at the next level, this all being color-coded. The box might be color-coded, as well as the bottles. Again, each of these bottles would be a single dose. Since they are all single-dose and contained within sterile bottles, the shelf life is considerably longer.

Figure 6:
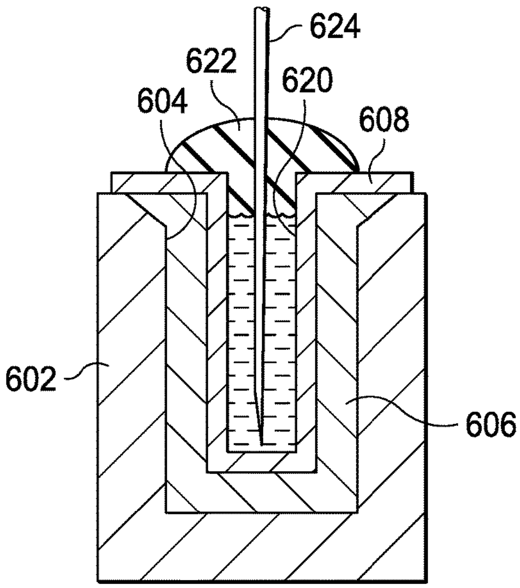
FIG. 6 illustrates a cross-sectional view of a low dose bottle.

Referring now to FIG. 6, there is illustrated a cross-section of a typical bottle that would be involved with respect to providing a single dose of 1 mL in a larger standard 5 mL bottle. A 5 mL bottle is represented by a bottle 602. This bottle 602 has an opening 604 that is provided for the 5 mL bottle. An insert 606 is provided for filling space within the bottle. This can be any type of plastic insert, etc. A smaller insert bottle 608 is disposed within the insert 606 to provide an elongated interior 620 which has a volume slightly in excess of 1 mL, such that a 1 mL dose can be disposed therein. This elongated interior is covered with a rubber stopper 622 such that a needle 624 can be disposed there through and be able to extract 1 mL of diluted antigen. If not for the elongated opening 620 facilitated by the insert 606 in the bottle 608, the 1 mL of diluted antigen would be disposed at a lower level and would be more difficult to extract.

Figure 7:
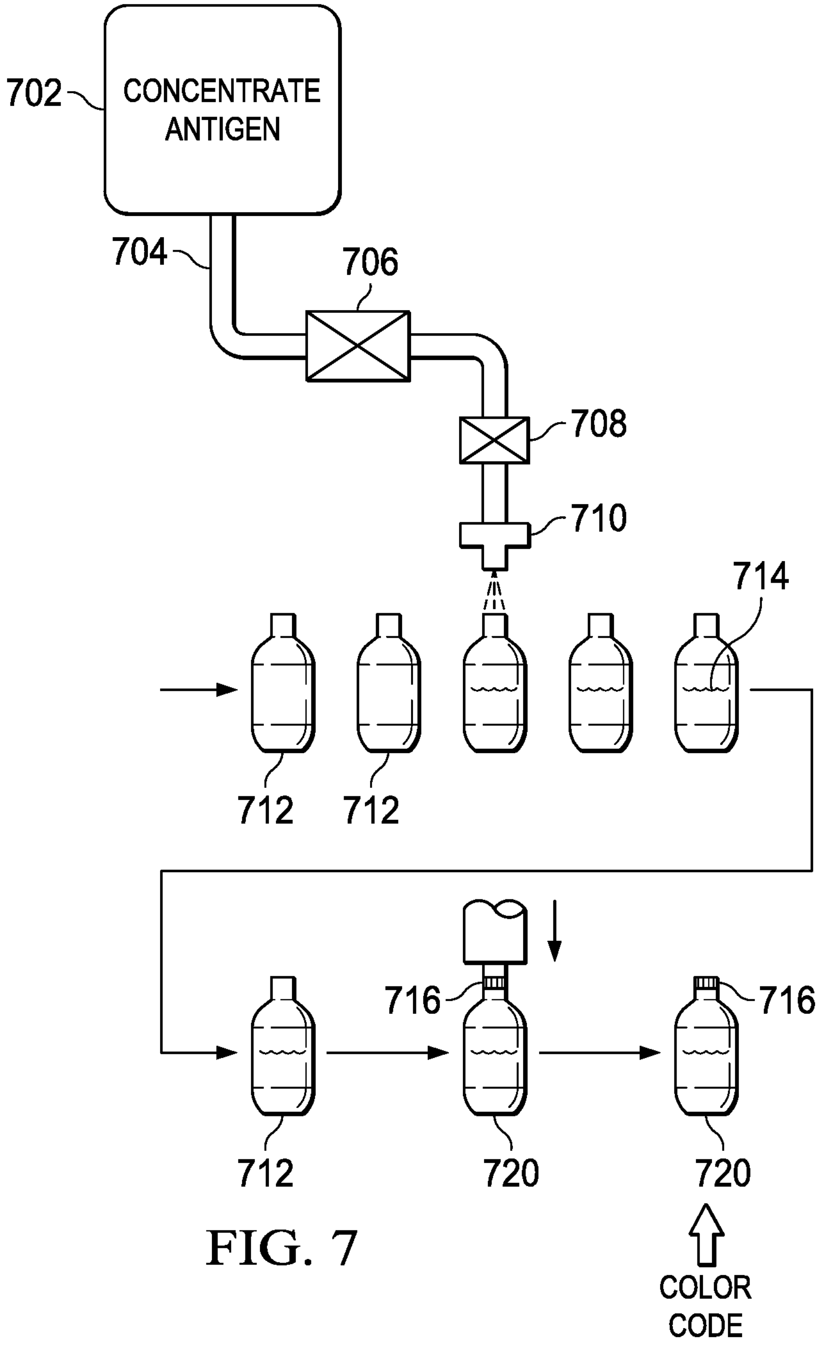
FIG. 7 illustrates a diagrammatic view of filling sterilized bottles with concentrated antigen.

FIG. 7 illustrates a diagrammatic view for filling sterilized bottles with concentrated antigen. For a particular antigen, a vessel 702 is provided containing the concentrated antigen which is fed through a tube 704 via a cut off 706 and a cutoff 708 to a dispensing nozzle 710, similar to the dispensing nozzles 224 described hereinabove. A plurality of empty sterilized bottles 712 that are passed along an assembly line underneath the nozzle 710, which dispenses a predetermined amount of concentrated antigen therein. This results in a plurality of the bottles 712 with a dispensed amount 714 of antigen disposed therein. These bottles 712 can range in size from a 0.5 mL bottle to a 10 mL bottle. The preferred size is approximately 5 mL. This, of course, depends upon the application, as will be described hereinbelow.

The next step in the process is to bottle 712 with a rubberized stopper 716, as described hereinabove with respect to FIG. 2. This results in a sterilized bottle 720, noting that the entire process is carried out in a sterile environment. At this point, the rubberized stopper 716 on the filled bottle 720 is covered with a layer foil to basically provide an overall sterile vessel. As noted hereinabove, to use this bottle 720 after sterilization, all that is required is to peel away the foil top and insert the needle through the rubberized stopper 716. At this point, of course, the bottle 720 will be in an unsterile environment. Thus, the first puncture with a sterile needle into the rubberized stopper 716 will be a sterile operation. Thereafter, a sterile environment cannot be ensured. At this point, as will be described hereinbelow, the bottle 720 is labeled or color-coded. Since this bottle 720 will be disposed in a kit, is important that there be some indicia provided that will allow the antigen contents of the bottle to be discriminated from the contents of the other bottles with different antigens disposed therein. This indicia can be an alpha character, a numeric character, a color reader barcode.

Figure 8:
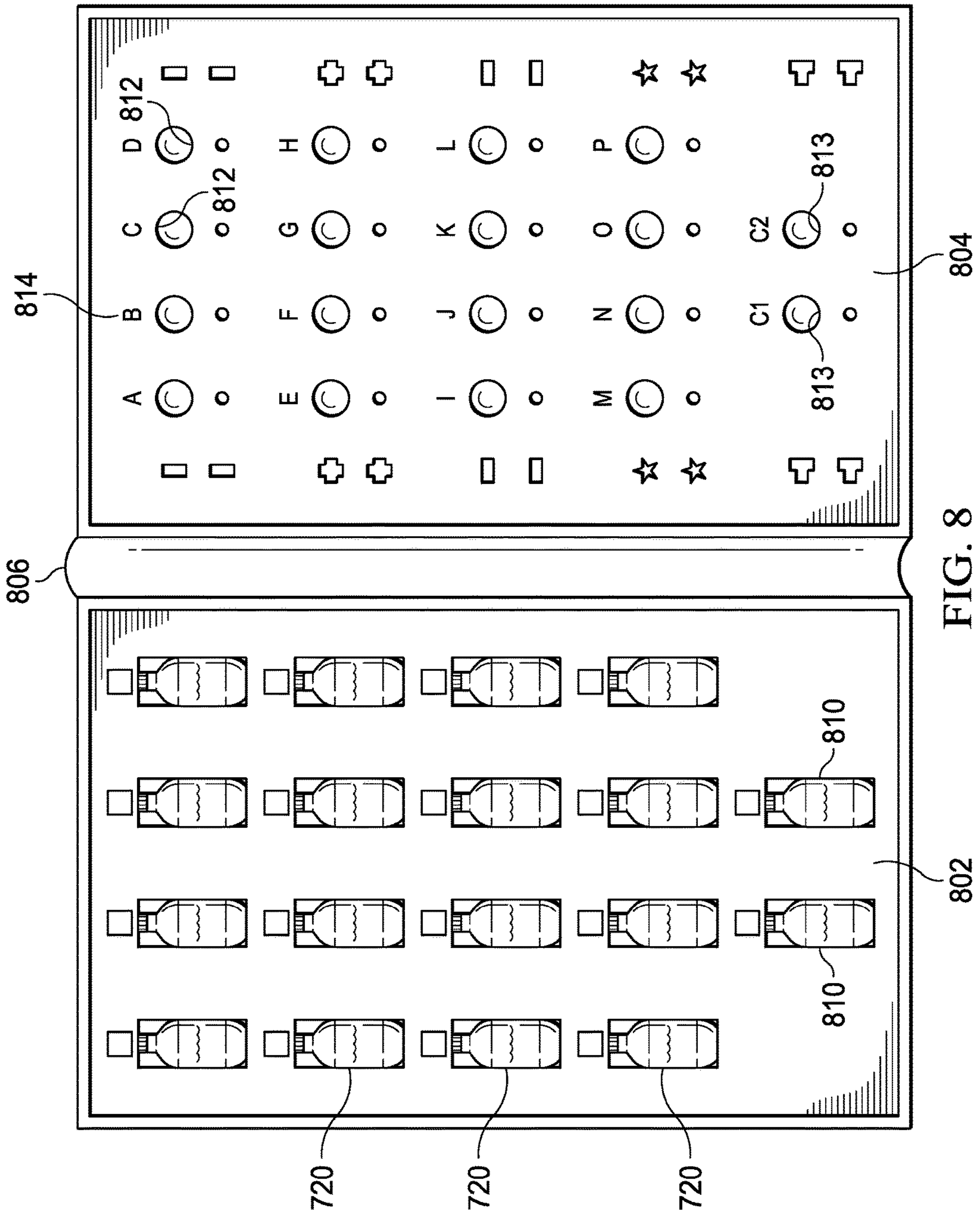
FIG. 8 illustrates a top view of a testing kit illustrating the concentrated antigen and the prick test wells.

Referring now to FIG. 8, there is illustrated a top view of a clamshell configuration having two portions, a portion 802 and a portion 804. These are joined together by a hinge 806 such that the clamshell configuration can be closed. The portion 802 is operable to contain a plurality of discrete antigens in bottles 720. There are also provided two bottles 810 that are control bottles. One of the bottles will contain water and the other will contain a histamine. The water, as the control, applied to the skin should elicit no response whereas the histamine, when applied to the skin, will elicit a guaranteed response. This provides the medical technologist some type of benchmark for the particular individual.

Figure 9:
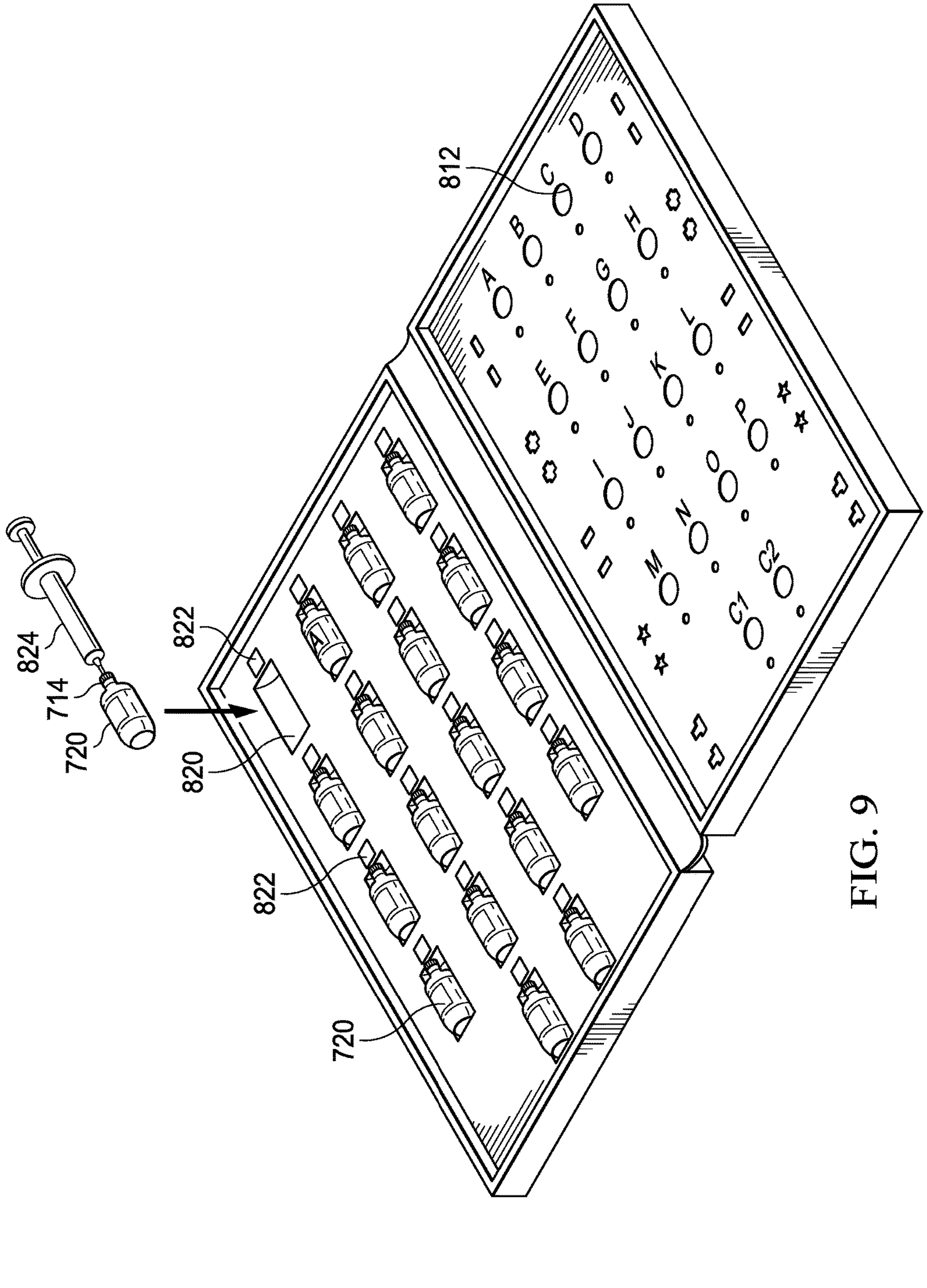
FIG. 9 illustrates a diagrammatic view of the operation of transferring concentrated antigen from one of the concentrated antigen bottles in the kit to an associated well in the kit.

The other side 804 constitutes a portion that contains a plurality of wells 812 that have disposed therein a very small portion, a drop or two, of antigen, wherein each of the wells 812 is associated with the corresponding bottle 720 with an antigen. Above each well 812 is provided an indicia marker 814 which is associated with the indicia on each of the bottles. It can be that the indicia is provided not only on the bottle but also on the insert associated with the bottle 720 in the portion 802. Thus, as illustrated in FIG. 9, a particular bottle 720 is retrieved from a well 820. Again, this well could have an indicia 822 disposed thereabove that is associated with a particular antigen for a particular kit. A hypodermic 824 is utilized to extract a portion of the antigen disposed within the bottle 720 through the rubberized stopper 716 after the foil is removed therefrom, and this extracted antigen is disposed within a corresponding well 812. Again, with color coding, it is possible to have the bottle coded for a certain color, the receiving pocket 820 color-coded for that bottle, and the well 812 associated therewith color-coded for that antigen. In such a manner, when the antigens are assembled for a particular kit, it is possible to ensure that the appropriate antigen is inserted in the appropriate pocket 820 by matching the colors, and, when utilizing the antigen to fill the well for a prick test, it can be ensured that the appropriate color coding is matched, since the bottle itself will have color coding disposed thereon. Again, an alpha character or numeric character could be utilized in the same manner.

Figure 10:
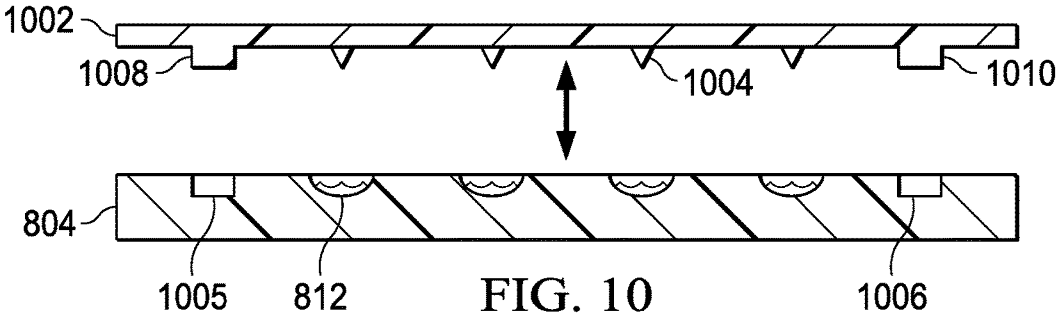
FIG. 10 illustrates a side cross-sectional view of the wells after antigen is disposed therein and illustrating applying the antigen in the wells to the tips of a prick tester.

As can be seen from FIG. 9, all that is required for the medical technologist is to open up a particular clamshell prick test kit and utilize the appropriate concentrated antigen for dispensing in the well 812, this dispensing requiring 1, 2 or 3 drops—a very small amount. Thereafter, as illustrated in FIG. 10, a prick tester 1002 is provided having a plurality of needles 1004 extending thereon and aligned with at least a row of wells 812. This protector 1002 is disposed there over and the edges aligned with alignment slots 1005 and 1006, there being a corresponding alignment tab 1008 and 1010 on the prick tester 1002 to ensure that needles 1004 are correctly aligned with the center of the well 812. When the prick tester 1002 is disposed down over the portion 804 and the tabs 1008 and 1010 are aligned and inserted within the slots 1005 and 1006, respectively, the tips of the needles 1004 will be sufficiently disposed within the corresponding well 812 in order to ensure that the tip of the needle has concentrated antigen disposed thereon. This is then applied to the skin of the patient to elicit the potential response thereto.

Figure 11:
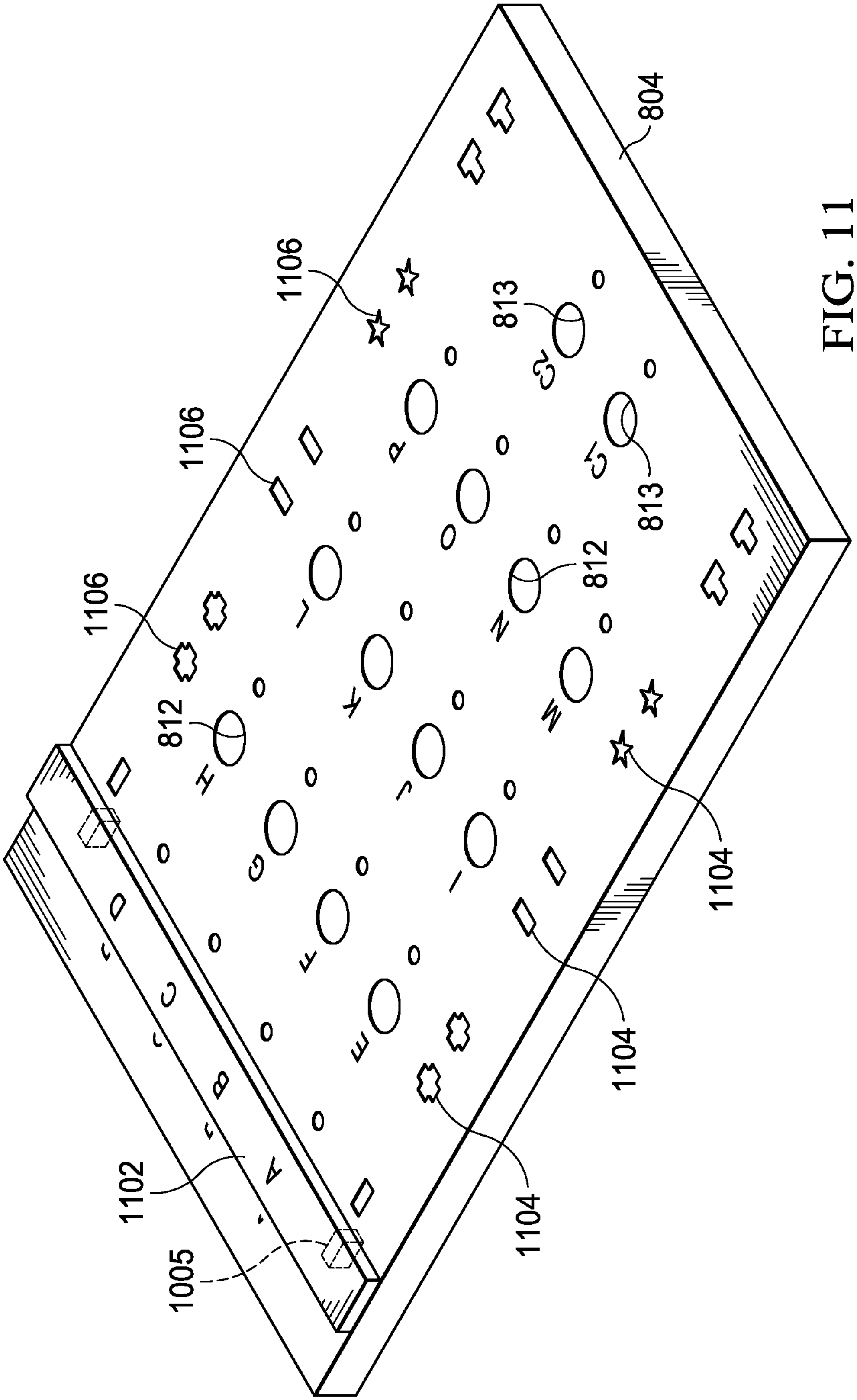
FIG. 11 illustrates a perspective view of the wells after filling in the disposal of a prick tester over a select ones of the wells.

Referring now to FIG. 11, there is illustrated a perspective view of the portion 804 having associated therewith the wells. In this portion, each of the wells 812 are disposed in rows, there being four rows each having four wells 812. Below those four rows are provided a single row for the two control wells 813. There is illustrated one configuration of the prick tester which allows a single row of wells 812 to be accessed. In this embodiment, a prick tester 1102 is provided that only accesses one row of wells and is disposed thereover with, in an exemplary embodiment, an indicia of an alpha character, A, B, C and D. Disposed thereunder will be a corresponding well 812 with the corresponding alpha character. The tab 1005 will align with the corresponding slot in the portion 804 associated with that row. It is noted that there will be provided a separate prick tester 1102 for each of the rows with corresponding matching alpha characters. In order to ensure that the prick tester will only be insertable into the portion 804 for the associated row, different dimensioned slots 1104 will be provided on one side of the row and different dimensioned slots 1106 will be disposed on the opposite side of the room. Thus, the prick tester 1102 for each row will not only be designed to only be associated with that row, but it also has to be oriented in the correct direction such that the rows are correctly designated for a particular prick tester. It could be that the prick test 1102 could cover two rows or could cover all four rows or even all four rows 812 and the control wells 813 in the bottom row.

Figure 12:
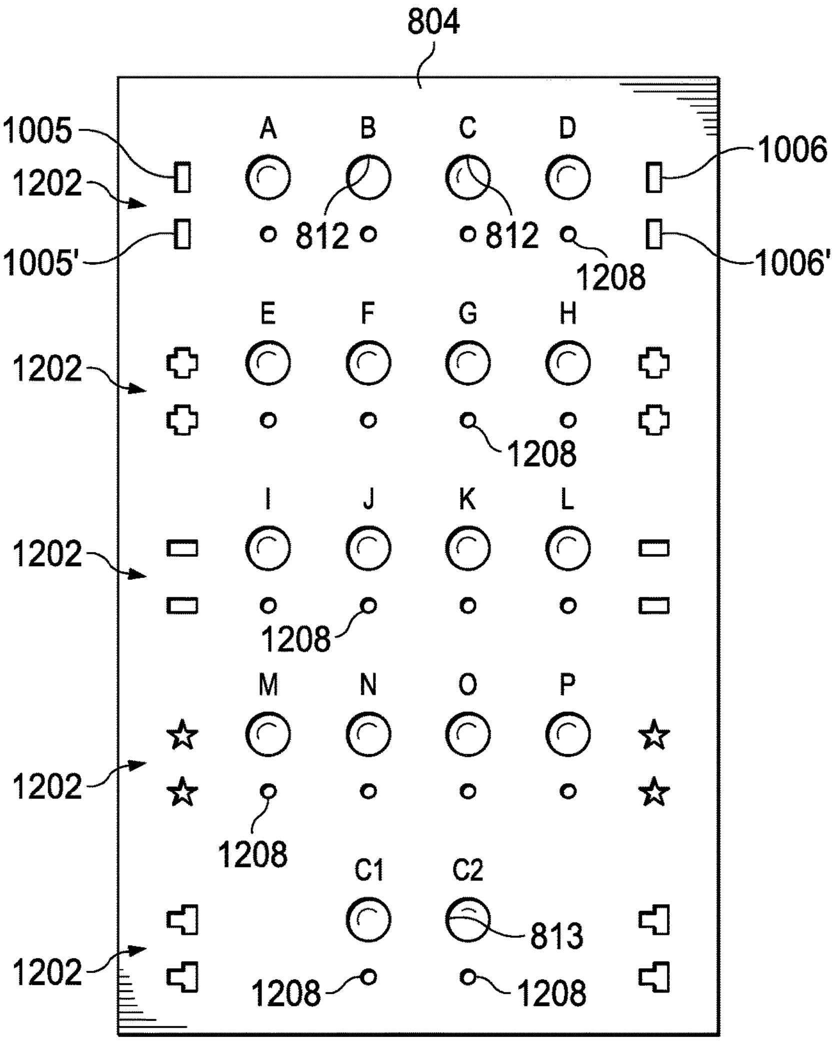
FIG. 12. Illustrates a top view of the embodiment of FIG. 11.

Referring now to FIG. 12, there is illustrated a top view of the portion 804 illustrating not only the wells 812 but also a storage region 1202 for each of the rows beneath the particular row. It will be a corresponding slot disposed in this particular storage region 1202, that storage region 1202 being a row in and of itself. Thus, for example, there will be a slot 1005 disposed on one side of the top row and a slot 1006 disposal the opposite side of each of the wells 812 in that row. Directly therebeneath, there will be a corresponding slot 1005' on one side of the storage region 1202 associated with that first row, and a corresponding slot 1006' disposed on the opposite side. There will be disposed directly beneath each well 812 a receiving hole 1208 for receiving the needle on the bottom of the associated prick tester.

Figure 13:
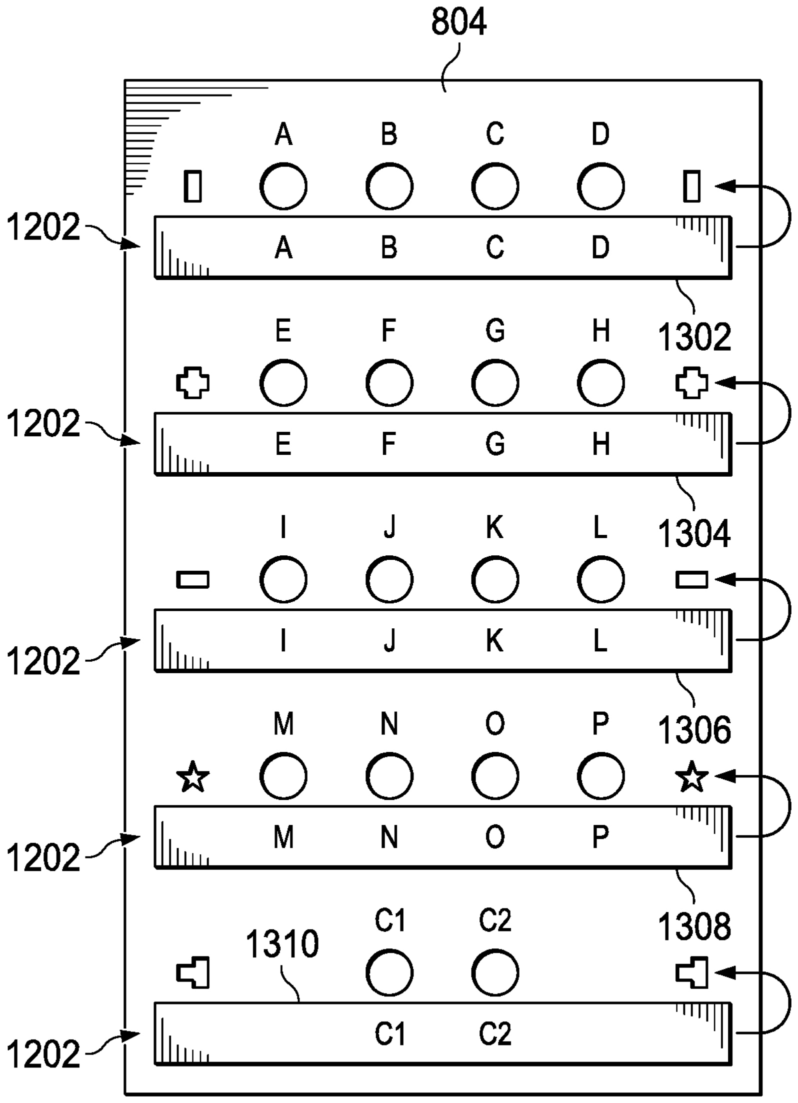
FIG. 13 illustrates a top view of a well portion of the kit with the protesters disposed thereon for storage.

Referring now to FIG. 13, there is illustrated a top view of the portion 804 in a shipping configuration. In this configuration, there will be provided a prick tester 1302 for the first row, a prick tester 1304 for the second row, a prick tester 1306 for the third row, a prick tester 1308 for the fourth row and a prick tester 1310 for the control row. Each of these is disposed in the respective storage region 1202 associated with each particular row. It is only necessary thereafter to remove the prick tester 1302 after concentrated antigen has been disposed within all or select ones of the wells in the first row to allow utilization thereof.

Figure 14:
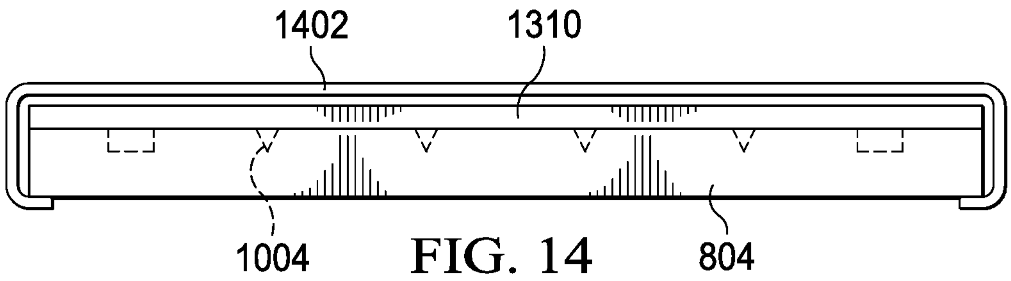
FIG. 14 illustrates a side view of the overall well portion and the stored prick tester with a sterile seal disposed thereon.

Referring now to FIG. 14, there is illustrated a side view of the portion 804 in the shipping configuration with the prick tester 1310 illustrated from the side. This is assembled in a sterile environment and, thereafter, it is sealed with a see-through seal 1402 that maintains the sterile environment. This can be removed when it is being used. Of course, there is no seal required over the antigen bottles 720 in the portion 802, as they are already sealed individually.

Figure 15:
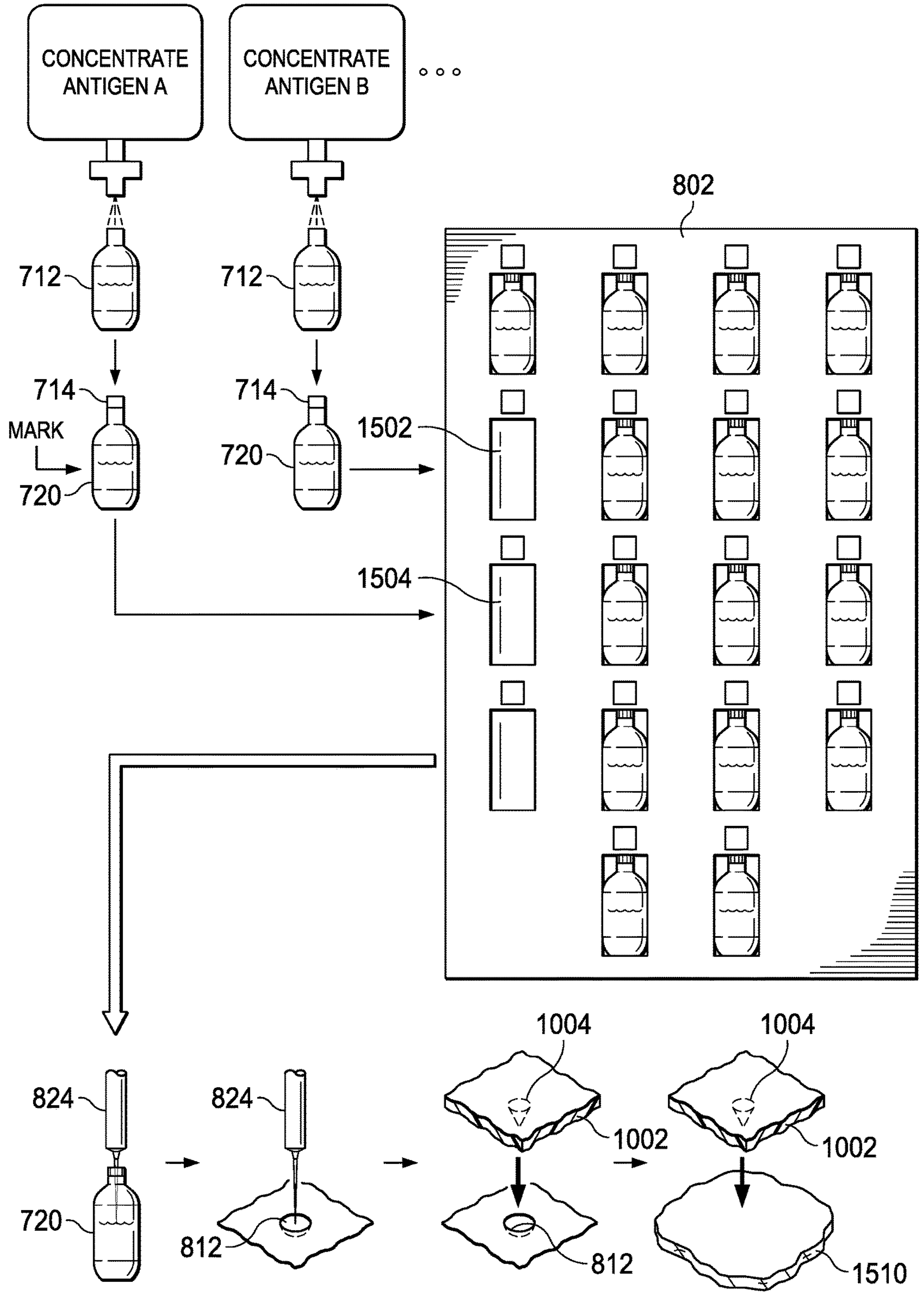
FIG. 15 illustrates a diagrammatic flow chart of the overall operation of assembling the kit and utilizing the kit.

Referring now to FIG. 15, there is illustrated a process flow illustrating the process of dispensing the concentrated antigen into the bottles 712 and then sealing them to provide the final bottle 720 with the rubberized stopper 716 disposed thereon. These are then each marked with the appropriate indicia. There can be a procedure wherein each antigen has a unique color associated there with some type of unique code. Due to the large number of antigens, it may be that two colors would have to be provided to provide discrimination among a large number of antigens. However, for standardized kits that require a finite number of antigens, this may not be necessary. If a large number of kits of a particular regional nature are assembled, it can be that the concentrated antigens are color-coded for those kits and maintained in an identified area. They can then be assembled into the kits as necessary. This is illustrated with directional arrows indicating that, for example, two wells 1502 and 1504 have bottles 720 disposed therein associated with antigen A and antigen B, respectively, for example. These are not necessarily directly disposed therein after filling but, rather, could be filled from a queuing station. The control bottles would, of course, be fairly standardized and may even have a standardized color across all kits. The next step is to then extract antigen from the select one of the bottles 720 and dispose it within a corresponding well 812. The prick tester 1002 and the pin 1004 associated with that well 812 will then be mated to coat the tip of needle 1004 with the small amount of antigen that was disposed in the well 812. This is then applied to the skin 1510 of a patient.

Figure 16:
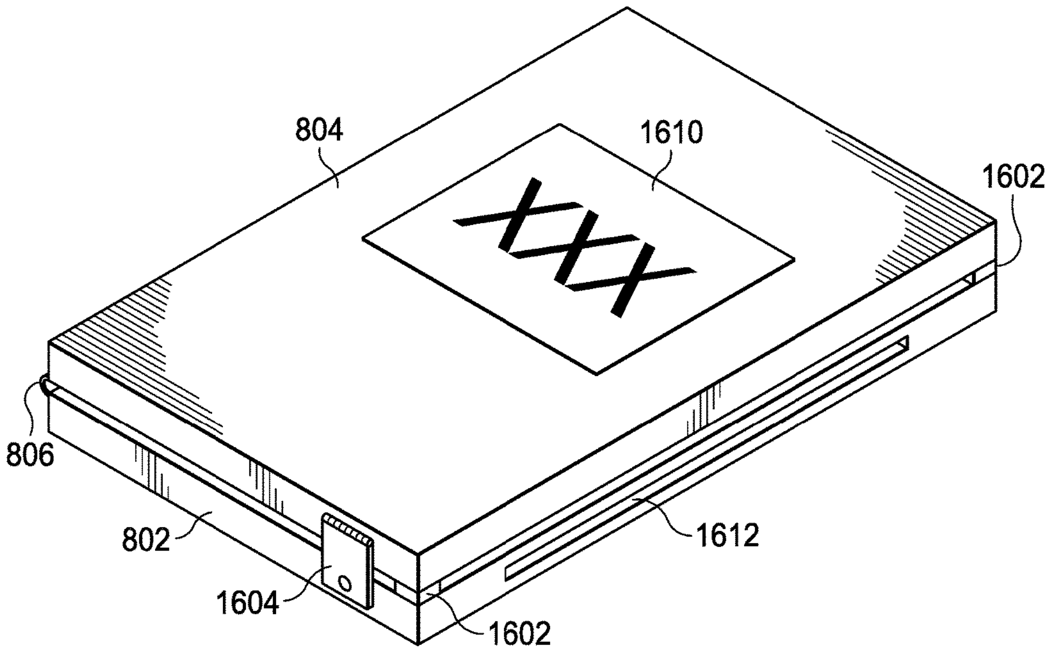
FIG. 16 illustrates a diagrammatic view of the kit and a close configuration.
Figure 17:
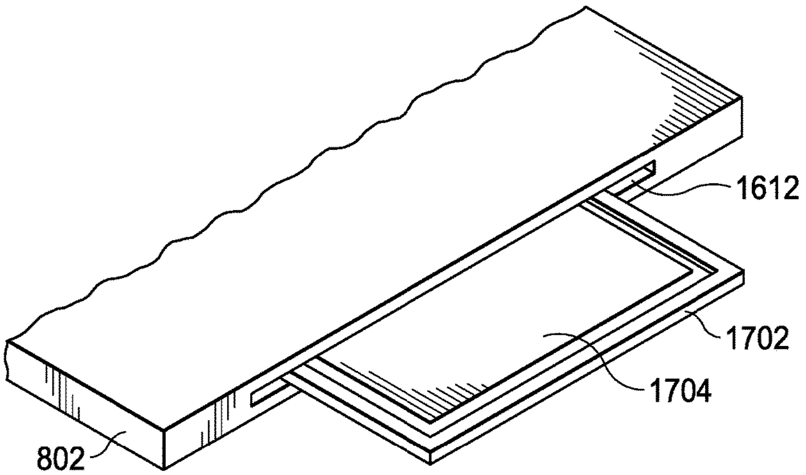
FIG. 17 illustrates a detailed view of a drawer for the information sheet.

Referring now to FIG. 16, there is illustrated a closed view of the clamshell configuration of the two portions 802 and 804. They will be disposed such that they will come together and be slightly separated with tabs 1602. A securing latch 1604 is disposed alongside to secure the two portions 802 and 804 together facing each other. There will be a label 1610 disposed on the upper side thereof identifying the particular point. In addition, there will be provided, in one example, and information slot 1612 within the portion 802, although it could be in the portion 804 or disposed any place with respect to the overall clamshell configuration. A detail of this information slot 1612 is illustrated in FIG. 17. This is illustrated as a drawer 1702 that can be pulled out with an information brochure 1704 disposed therein. This information brochure could contain advertisements, instructions and also well maps for the various wells indicating the antigens that are disposed therein for this particular kit. There are also be provided safety instructions and emergency numbers and the such.

Figure 18:
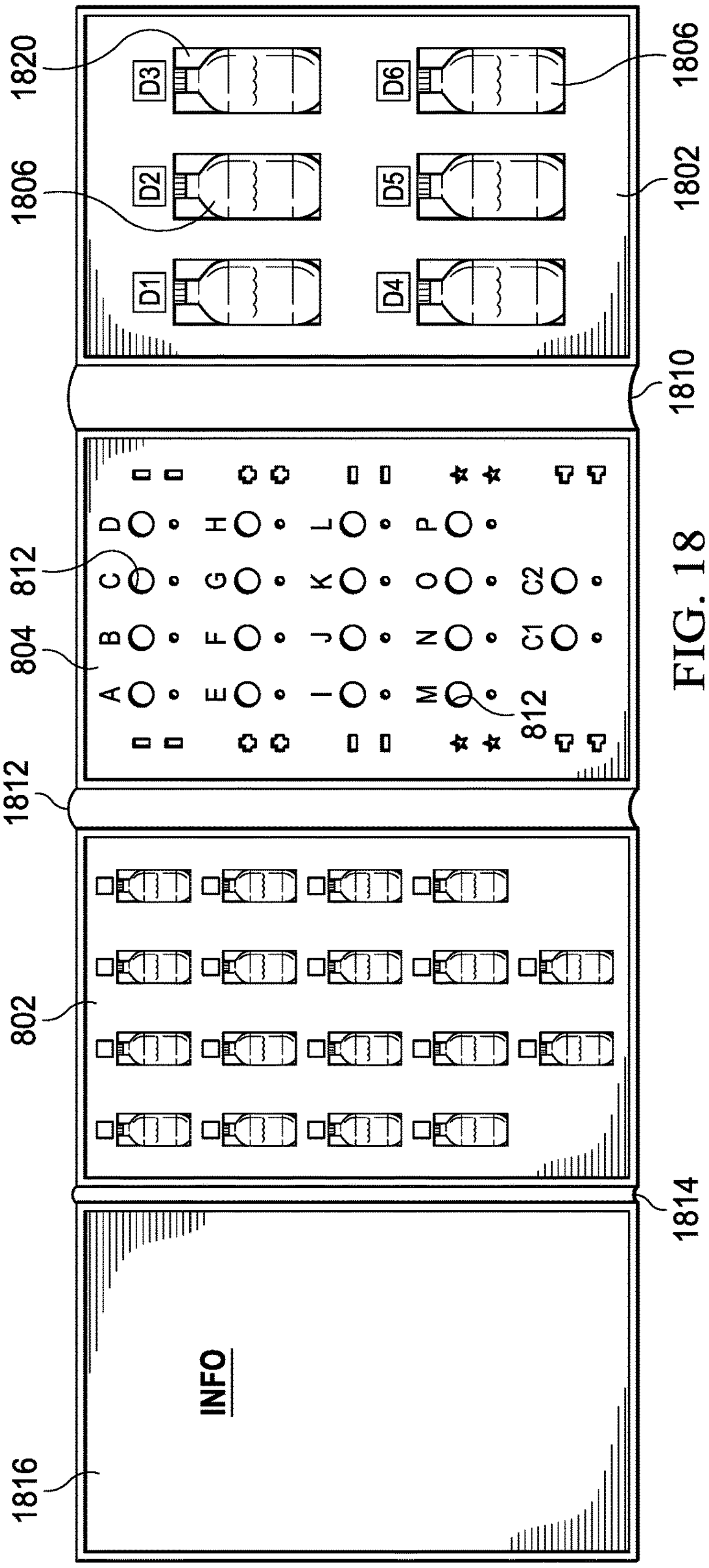
FIG. 18 illustrates an exploded view of the kit with the addition of a dilutant addendum.
Figure 19:
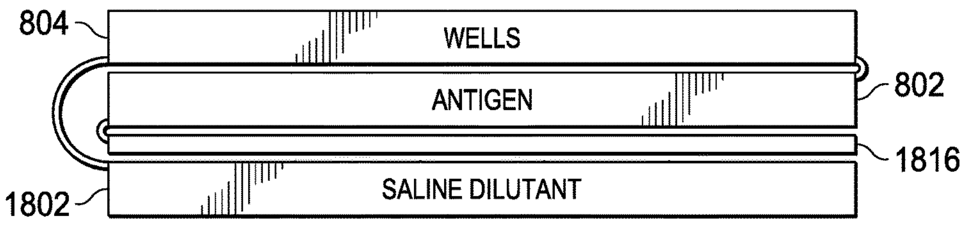
FIG. 19 illustrates a side view of the fully closed kit.

Referring now to FIG. 18, there is illustrated a view of an open clamshell with an addendum section 1802 attached thereto. This addendum section 1802 has disposed therein a dilutant set of saline bottles 1806, although they could contain other dilutants that are useful for the dilution operation, as described hereinabove. This is hinged to the side of the portion 804 by a hinge 1810. Additionally, the information section is disposed in a section attached by a hinge 1814 to a section 816 that is foldable. When this entire system is folded into a multiple level clamshell configuration, the configuration is as illustrated in FIG. 19.

Figure 20:
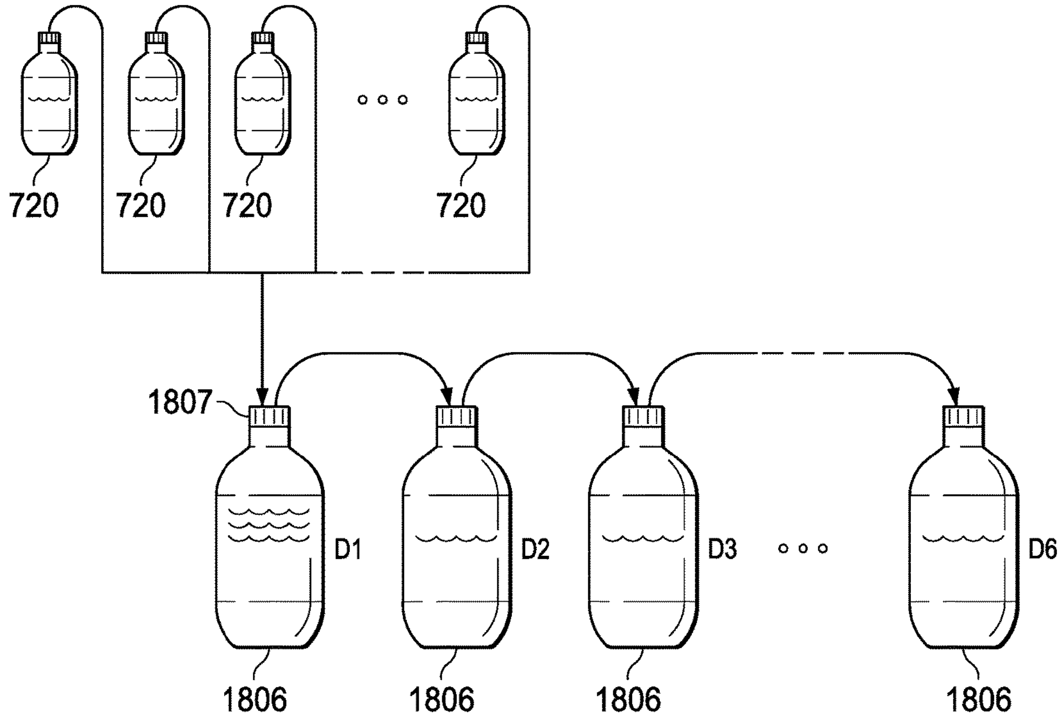
FIG. 20 illustrates the dilution process in a stepwise sequence.

FIG. 20 illustrates a diagrammatic view of the operation of creating a set of diluted antigens in accordance with a therapeutic regimen provided as a prescription. In accordance with the operation of the kit, the first step is to determine the sensitivity of a particular individual to one or more of the antigens disposed in the kit. This is the "testing" phase. Once it is determined which antigens elicit a response, a cocktail can then be created. This cocktail of antigens is facilitated by selecting the first bottle 1806 from section 1802. As noted in FIG. 18, each of the bottles 1806 is disposed within a well 1820. Above each of these wells is disposed a designator D1-D6. These are associated with the dilution level of a particular model. Each of these bottles has contained therein a predetermined amount of saline solution. The typical procedure, as described hereinabove, is to first mix concentrated antigen within the first bottle 1806 from select ones or more of the antigen bottles 720. This is facilitated with a hypodermic needle. The same hypodermic needle could be utilized for each extraction, but there may be some issue with sterility and a separate hypodermic needle could be utilized for each extraction. This is up to the medical technologist. A predetermined amount of concentrated antigen is extracted from the associated antigen bottle 720 that elicited a response during the prick test in the testing phase and is then inserted into the bottle 1806 through the associated stopper 1807 on each bottle 1806. The bottle D1 is initially filled with approximately 8 mL of saline solution or similar dilutant. The bottle is a 10 mL bottle. To achieve the appropriate dilution level in the bottle 1806, the instructions will inform the medical technologist how much dilutant to extract from each of the bottles. In one example, a level of 0.2 mL could be extracted, allowing 10 extractions to be inserted within the bottle 1806. If all 12 bottles were utilized, this could result in 2.4 mL of concentrated antigen from 12 bottles 720 be inserted into the bottle 1806. Thus the bottle 1806 could be filter level of 7.6 mL of dilutant initially. This resulted in an initial level of 7.6 mL filled potentially to 10 mL. A finite amount of dilutant is extracted from the bottle 1806 labeled D1 and transferred to the second bottle 1806 labeled D2 and so on until the last transfer to the bottle 1806 labeled D6. This will be a final bottle. These bottles could also be color-coded or marked with the particular dilutant level such that they could be placed back into the kit. The reason for this is that a therapeutic program would require a patient to initially receive injections from the highest diluted bottle 1806, associated with the level D6 in three or four doses or more of 0.5 mL each. The patient would then move on to the higher next higher diluted level and so on. This was described hereinabove. Thus, to recap, the procedure is to provide a test kit to a pharmacy which could then be distributed to a medical technologist. This kit can provide all of the antigens necessary to perform the prick test and the tools to facilitate that testing operation in the testing phase. If this was just a prick test kit and did not require any dilution process, only a small bottle would be required, on the order of possibly 0.5 mL or 1 mm. Thus, the bottle 720 could be very small. However, by providing the dilutant section 1802 in the clamshell with the dilutant bottles, larger bottle 720 could be facilitated to include a higher level of antigen for the purpose of creating a dilution set. Again, these could be as high as 5 mL or 10 mL. In some situations, a 10 mL bottle 720 may be facilitated really due to the fact that that is the industry standard. However, the size of the bottle merely reflects the amount required to, first, perform the prick test and, second, create the dilution sets. Since only 0.2 mL is required to create the dilution sets from anyone bottle 720, it may be that a small bottle of lesson 1 mL could be utilized. The clamshell configuration therefore provides an entire solution to either just the prick test or a combination of the prick test and the dilution set creation. Thus, a diagnosis can be performed and then a prescription created and filled all with a single kit.

Figure 21A:
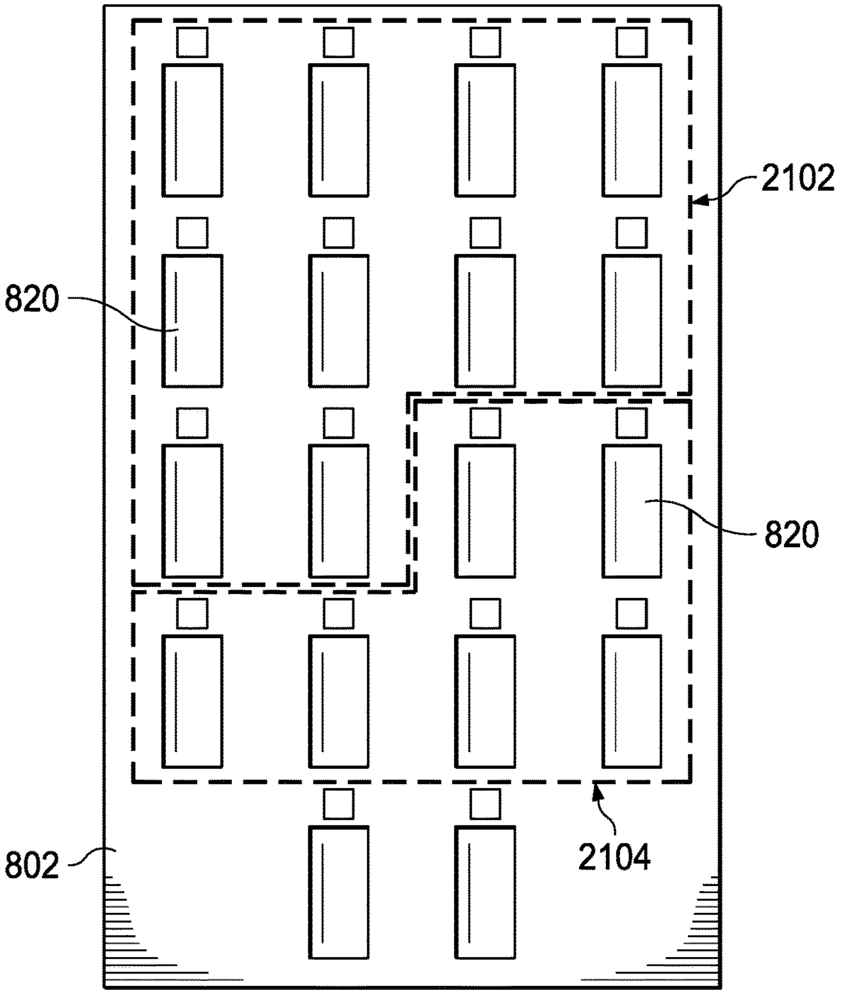
FIGS. 21A-21C illustrate top views of different types of kits for standardized antigens and region specific antigens and the various assemblies.
Figure 21C:
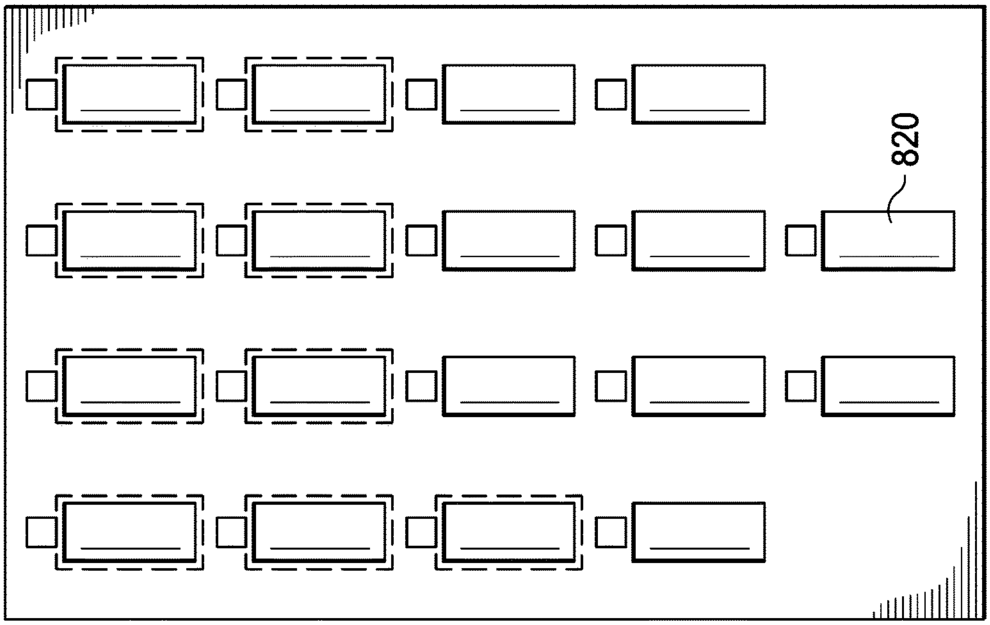
Figure 21B:
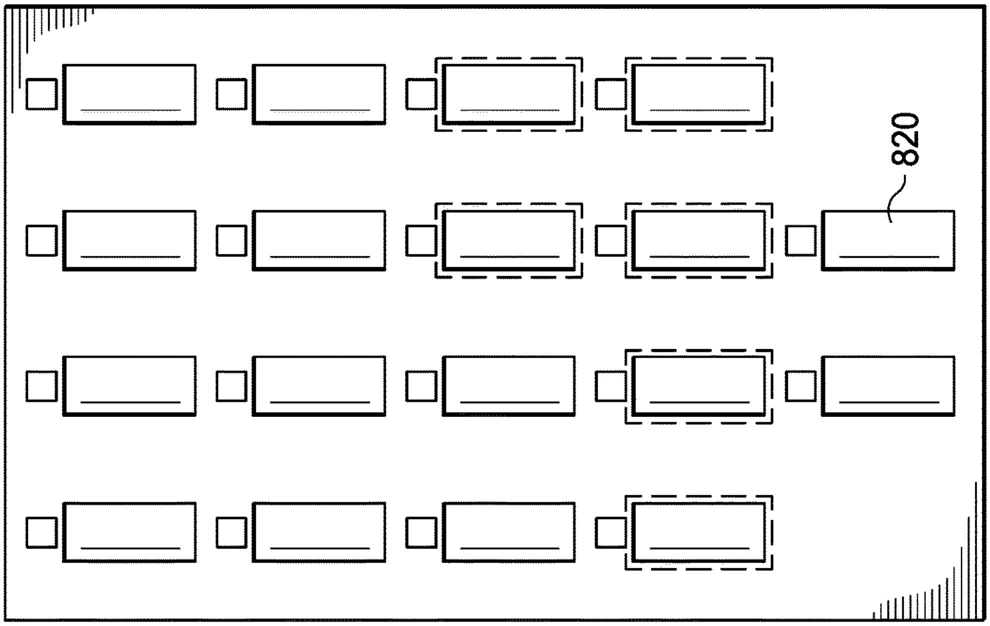

Referring now to FIG. 21A, there is illustrated a top view of a first section 802 having disposed to sections therein. There are provided eight wells 820 associated with a standardized section 2102 and 7 wells 820 associated with a region specific section 2104. The reason for this is that the kits can be "regionalized." This will allow a particular kit to be provided to a given region, wherein standardized antigens could be provided which are utilized over all regions and region specific antigens can be provided for a particular region and even a particular season in that region. The controls will be common across all kits. FIG. 21B illustrates a second configuration which is just standardized antigens. It can be seen less than 12 antigens might be included in this kit, as illustrated in un-dashed wells 820. Similarly, there can be provided a regional kit illustrated in FIG. 21C wherein only the wells 820 that are un-dashed are filled.

When the kits are originally assembled, each of antigens has an NDC associated therewith. When all of the antigens are assembled into a "testing" kit, a separate NDC is associated with that kit. This particular NDC associated with that kit is an approved NDC such that it will be reimbursed by insurance. It is for the purpose of testing. By including the dilutant section 1802 in the testing kit, the NDC will still be associated with a "testing" kit and, therefore, it will be reimbursed as such. Even though it may be utilized to fill the prescription, it is still a "testing" kit. Additionally, each kit, regardless of what the purpose of it is, can have an NDC associated therewith and still be a testing kit. Thus, each regional kit will have NDC, each standardized kit will have NDC, and each combines standardized/regional kit will have NDC. In general, the term "regional kit" will refer to the kit that provides both standardized and regional antigens. The regional-only kit referred to as "regional-only."

Figure 22:
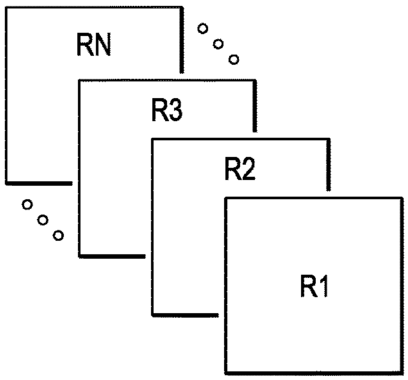
FIG. 22 illustrates a detailed view of the various regional kits.
Figure 23:
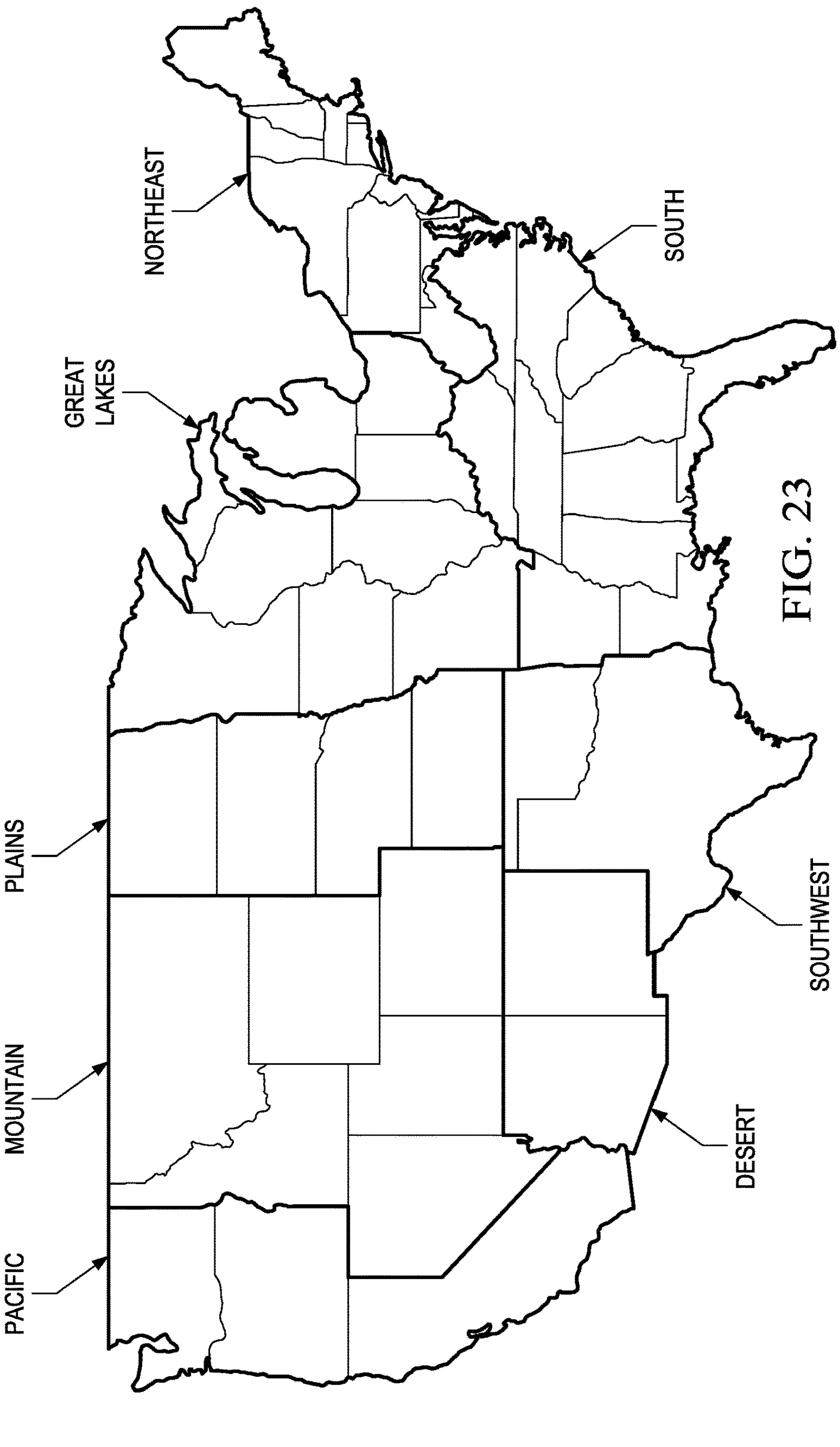
FIG. 23 illustrates a mapping view of the United States with the various allergy regions.

A group of regional kits can be provided, as illustrated in FIG. 22, one for each region that has defined issues. FIG. 23 illustrates a map of the United States and various regions that have differing requirements. They are the Pacific region, the Desert region, the Mountain region, Southwest region, the Plains region, the Great Lakes region, the South region and the Northeast region of the country. In the Pacific region, for example, trees usually pollinate from February to June. Trees that produce pollen that may trigger nasal allergy symptoms are cedar, walnut, and rye. Other trees that may cause nasal allergy symptoms in this region are Hazel, Juniper, Alder, Ash, Burch, Box Elder, and Oak. Grasses generally pollinate from March to November in this region. Some of the most common grasses that can trigger seasonal nasal allergy symptoms are sweet vernal, fescue, bluegrass, Bermuda grass, brome, orchard, quack grass, wheat grass, and redtop. The weed season for the region generally lasts from April to November, including ragweed, chenopod, and sage. Other weeds that can trigger nasal allergy symptoms include pigweed, iodine bush, saltbush, lamb's quarter, Mexican fire bush, and Russian thistle.

In the Mountain region, trees usually pollinate from March to May. The trees that can trigger nasal allergy symptoms include the cedar, maple, and oak. Other trees that may trigger nasal allergy symptoms are the box elder, alder, birch, juniper, oak, and ash. Grasses pollinate from April to July in this region. Some of the grasses that can cause nasal allergy symptoms include quack grass/wheat grass, redtop, brome, Bermuda grass, and orchard grass. Weeds take over from early June through October, including ragweed, tumbleweed, and chenopod. Other weeds that are allergens or trigger nasal allergy symptoms include waterhemp, pigweed, iodine bush, saltbush/scale, sugarbeet, lamb's quarter, Mexican fire bush, and Russian thistle. In the Desert region, cedar, ash, and oak pollinate from February to April. Other trees that can trigger nasal allergy symptoms include cypress, mesquite, ash, and olive. The grass season for this region can last from April until October. Some of the grasses that can cause nasal allergy symptoms include brome, Bermuda, salt grass, rye, Canary grass, and June grass. Weeds in the region pollinate from March to December, including ragweed, chenopod, and sage. Other weeds that are allergens or trigger nasal allergy symptoms include carelessweed, iodine bush, saltbush/scale, lamb's quarter, and Russian thistle. In the Plains region, trees pollinate from March to May, including oak and cedar. Other trees that can trigger nasal allergy symptoms include alder, birch, maple/box elder, hazelnut, and oak. Grasses pollinate from late May to July in this region, including quack grass/wheat grass, redtop, brome, orchard grass, and rye grass. Weeds take over from July through September, including ragweed, plantain, and nettle. Other weeds that can trigger nasal allergy symptoms include water hemp, pigweed, lamb's quarter, Mexican fire bush, and Russian thistle. In the Southwestern region, cedar, elm, and oak begin pollinating in early January and end in June. Other trees whose pollen is a known allergen include box elder and mesquite. Elm trees begin pollinating in late January and end in April, while olive pollinates from mid-March to mid-April.

The grass season for this region usually begins in April and lasts until September. The primary grasses for the region that can trigger nasal allergy symptoms are Bermuda, quack grass/wheat grass, and redtop. Weeds in the region include ragweed, chenopod, and dock, which pollinate between July and October. Other weeds that can trigger nasal allergy symptoms include waterhemp, carelessweed/pigweed, saltbush/scale, and lamb's quarter. In the Great Lakes region, trees with pollen that can trigger nasal allergy symptoms are elm, maple/box elder, alder, birch, oak, and hickory. They can pollinate from March through June. Oak trees may continue pollinating until mid-June. Many grasses pollinate in this region during the summer, from May to July. Starting in May, redtop, brome, orchard grass, fescue, rye, Bermuda, and timothy pollinate. Weeds generally pollinate from July to September, including ragweed, plantain, and nettle. Other weeds that are allergens or trigger nasal allergy symptoms include waterhemp, lamb's quarter, pigweed, Mexican fire bush, and Russian thistle. Later in the season, hemp can trigger symptoms for people with seasonal nasal allergies—typically from mid-July to mid-August.

Then, from early August until late September, ragweed pollinates in this region. In this region, a variety of trees that can produce pollen that can trigger nasal allergy symptoms are pecan, oak, and cedar. Others include maple/box elder, birch, hickory, and oak. Grass pollens can pollinate nearly year-round in parts of this region. Some grasses that can trigger nasal allergy symptoms are Bermuda, saltgrass, bahia, redtop, vernal, orchard, rye, salt grass, fescue, and timothy. Among the weeds whose pollen can cause nasal allergy symptoms are ragweed, plantain, and nettle. Other weeds that are allergens or trigger nasal allergy symptoms are the lamb's quarter, sagebrush, English plantain, pigweed, waterhemp, and carelessweed. In the Northeast region, beginning in February and lasting until June, several types of trees in this region produce pollen that can trigger nasal allergy symptoms—particularly birch, maple/box elder, oak, juniper/cedar, and pine trees. From May to late August, grasses pollinate in the area including orchard, redtop, fescue, and timothy. Other grasses in the region that can trigger nasal allergy symptoms include vernal grass and Bermuda grass. From August to October, weeds such as ragweed, plantain, and nettle pollinate in this region. Other weeds that are allergens or trigger nasal allergy symptoms include lamb's quarter, cocklebur, pigweed, and Mexican fire bush.

It can be seen, therefore, that each region can have different requirements and each of these regional kits can be designed for a particular region and given as separate NDC code that can be reimbursable.

Although the preferred embodiment has been described in detail, it should be understood that various changes, substitutions, and alterations can be made therein without departing from the spirit and scope of the invention as defined by the appended claims.

What is claimed is:

1. A regional antigen testing kit, comprising:

a first portion having disposed therein a plurality of concentrated antigens, each one of the plurality of concentrated antigens being disposed in a sealable container, and the first portion further having disposed therein a first control material and a second control material, the first control material and the second control material each being disposed in a sealable container;

a second portion hingedly coupled to the first portion, allowing for the regional antigen testing kit to be opened and closed in a clamshell configuration, wherein the second portion includes a plurality of wells capable of receiving an amount of concentrated antigen;

visual indicia disposed on the first portion and the second portion, in order to correspond each of the plurality of concentrated antigens with one of the plurality of wells; and a third portion having disposed therein a plurality of sealable containers containing a dilutant.

2. The regional antigen testing kit of claim 1, wherein the dilutant comprises a saline solution.

3. The regional antigen testing kit of claim 1, wherein the dilutant comprises a glycerol solution.

4. The regional antigen testing kit of claim 1, wherein the first control material is water.

5. The regional antigen testing kit of claim 1, wherein the second control material is a histamine.

6. The regional antigen testing kit of claim 1, wherein the regional antigen testing kit includes a National Drug Code (NDC) associated with the regional antigen testing kit.

7. The regional antigen testing kit of claim 1, wherein the plurality of concentrated antigens is associated with a particular geographic area.

8. The regional antigen testing kit of claim 7, wherein the regional antigen testing kit includes one of a plurality of National Drug Codes (NDCs), the one of the plurality of NDCs being assigned to the antigen regional testing kit based on the particular geographic area.

* * * * *